(12) United States Patent
Bang et al.

(10) Patent No.: US 10,526,640 B2
(45) Date of Patent: Jan. 7, 2020

(54) METHODS FOR RETRIEVING SEQUENCE-VERIFIED NUCLEIC ACID FRAGMENTS AND APPARATUSES FOR AMPLIFYING SEQUENCE VERIFIED NUCLEIC ACID FRAGMENTS

(71) Applicant: INDUSTRY-ACADEMIC COOPERATION FOUNDATION, YONSEI UNIVERSITY, Seoul (KR)

(72) Inventors: Duhee Bang, Seoul (KR); Hwangbeom Kim, Seoul (KR); Namjin Cho, Seoul (KR); Hyeonseob Lim, Chungcheongnam-do (KR); Sangun Park, Seoul (KR); Hyojun Han, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 690 days.

(21) Appl. No.: 14/975,873

(22) Filed: Dec. 21, 2015

(65) Prior Publication Data
US 2016/0201052 A1    Jul. 14, 2016

Related U.S. Application Data

(63) Continuation-in-part of application No. PCT/KR2014/005439, filed on Jun. 19, 2014, and a continuation-in-part of application No. PCT/KR2015/000828, filed on Jan. 27, 2015.

(30) Foreign Application Priority Data

Jun. 19, 2013  (KR) .................. 10-2013-0070660
Jan. 28, 2014  (KR) .................. 10-2014-0010407

(51) Int. Cl.
*C12Q 1/6806* (2018.01)
*C12Q 1/6874* (2018.01)

(52) U.S. Cl.
CPC ......... *C12Q 1/6806* (2013.01); *C12Q 1/6874* (2013.01)

(58) Field of Classification Search
None
See application file for complete search history.

(56) References Cited

U.S. PATENT DOCUMENTS

2005/0130173 A1    6/2005  Leamon et al.

FOREIGN PATENT DOCUMENTS

| JP | 3640840 | 4/2005 |
|----|---------|--------|
| KR | 1020000050411 | 3/2002 |
| KR | 1020107020466 | 10/2010 |
| KR | 1020100027537 | 10/2011 |
| KR | 1020120084303 | 2/2013 |

OTHER PUBLICATIONS

Matzas et al., "High-fidelity gene synthesis by retrieval of sequence-verified DNA identified using high-throughput pyrosequencing," Nat. Biotechnol. 2010, 28:1291-1294. (Year: 2010).*
Rohland et al., "Cost-effective, high-throughput DNA sequencing libraries for multiplexed target capture," Genome Res. 2012, 22: 939-946, published online Jan. 20, 2012. (Year: 2012).*
Maricic et al., "Multiplexed DNA Sequence Capture of Mitochondrial Genomes Using PCR Products," PLoS ONE 2010, 5(11): e14004. (Year: 2010).*
Matzas et al., High-fidelity gene synthesis by retrieval of sequence-verified DNA identified using high-throughput pyrosequencing, Nature Biotechnology, Dec. 2012, pp. 1291-1295, vol. 28, No. 12, Nature America, Inc. Abstract.
Metzker, Sequencing technologies—the next generation, Nature Reviews, Genetics, Jan. 2010, pp. 31-46, vol. 11, Macmillan Publishers Limited. Abstract.
Kim et al., 'Shotgun DNA synthesis' for the high-throughput construction of large DNA molecules, Nucleic Acids Research Advance Access, Jun. 16, 2012, pp. 1-8, Oxford University Press. Abstract.

* cited by examiner

*Primary Examiner* — Kaijiang Zhang
(74) *Attorney, Agent, or Firm* — STIP Law Group, LLC

(57) ABSTRACT

A method for retrieving nucleic acid fragments, including: providing reduced DNA libraries during sequencing; amplifying nucleic acid fragments from the reduced DNA libraries; and retrieving the amplified nucleic acid fragments. The method further includes acquiring desired nucleic acid fragments among the retrieved nucleic acid fragments. The desired nucleic acid fragments are acquired using sequences having a homology to the barcode sequences, when the amplified nucleic acid fragments are tagged with specific barcode sequences.

3 Claims, 16 Drawing Sheets

Specification includes a Sequence Listing.

[Fig. 1]
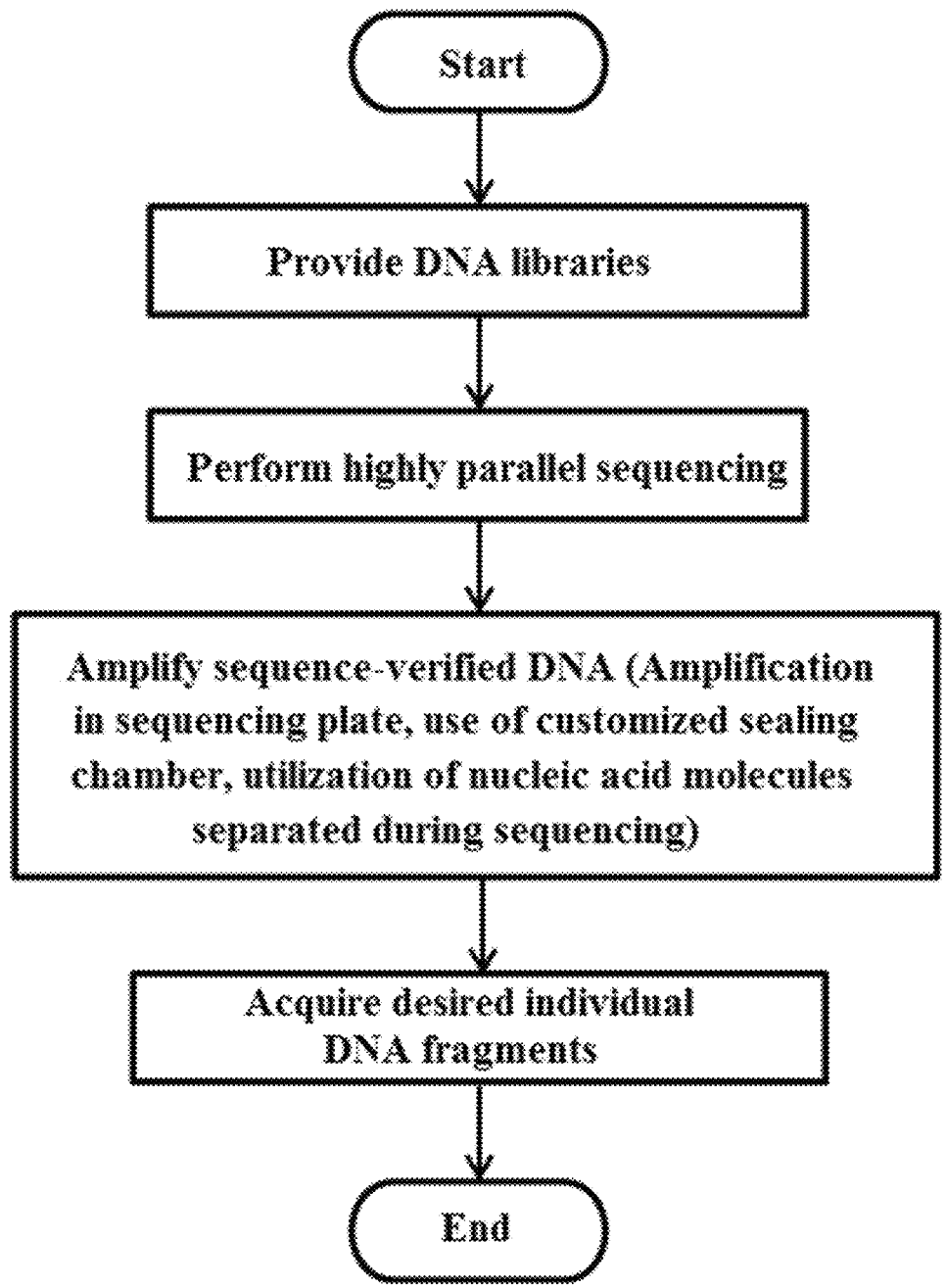

[Fig. 2]
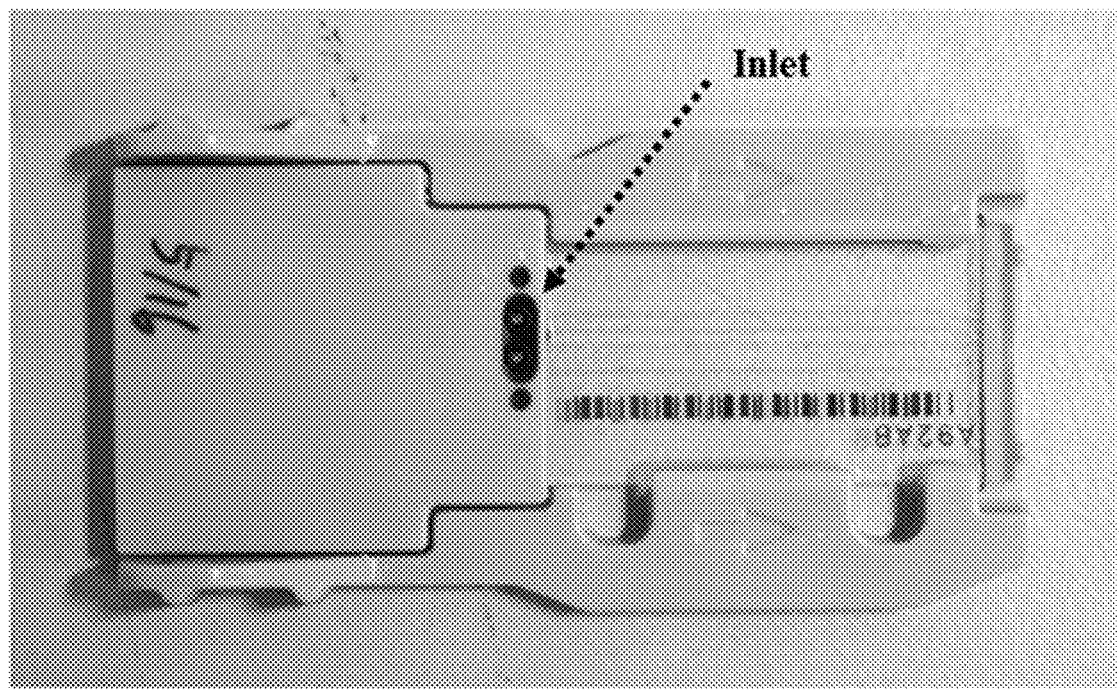
Before sealing
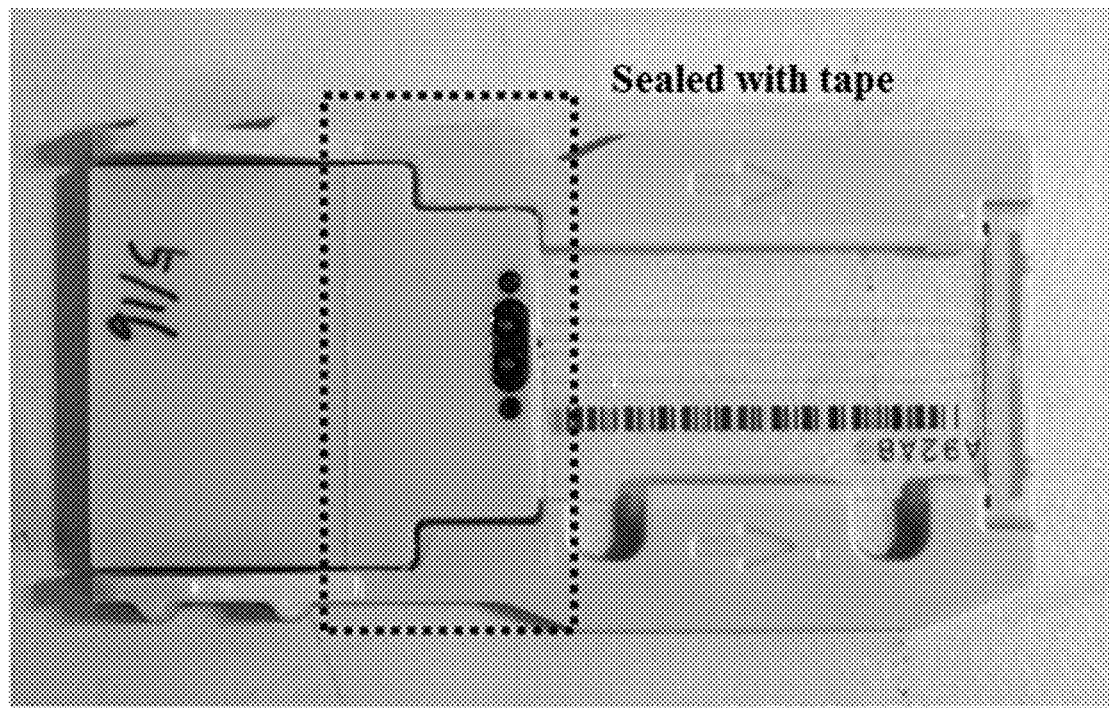
After sealing

[Fig. 3]
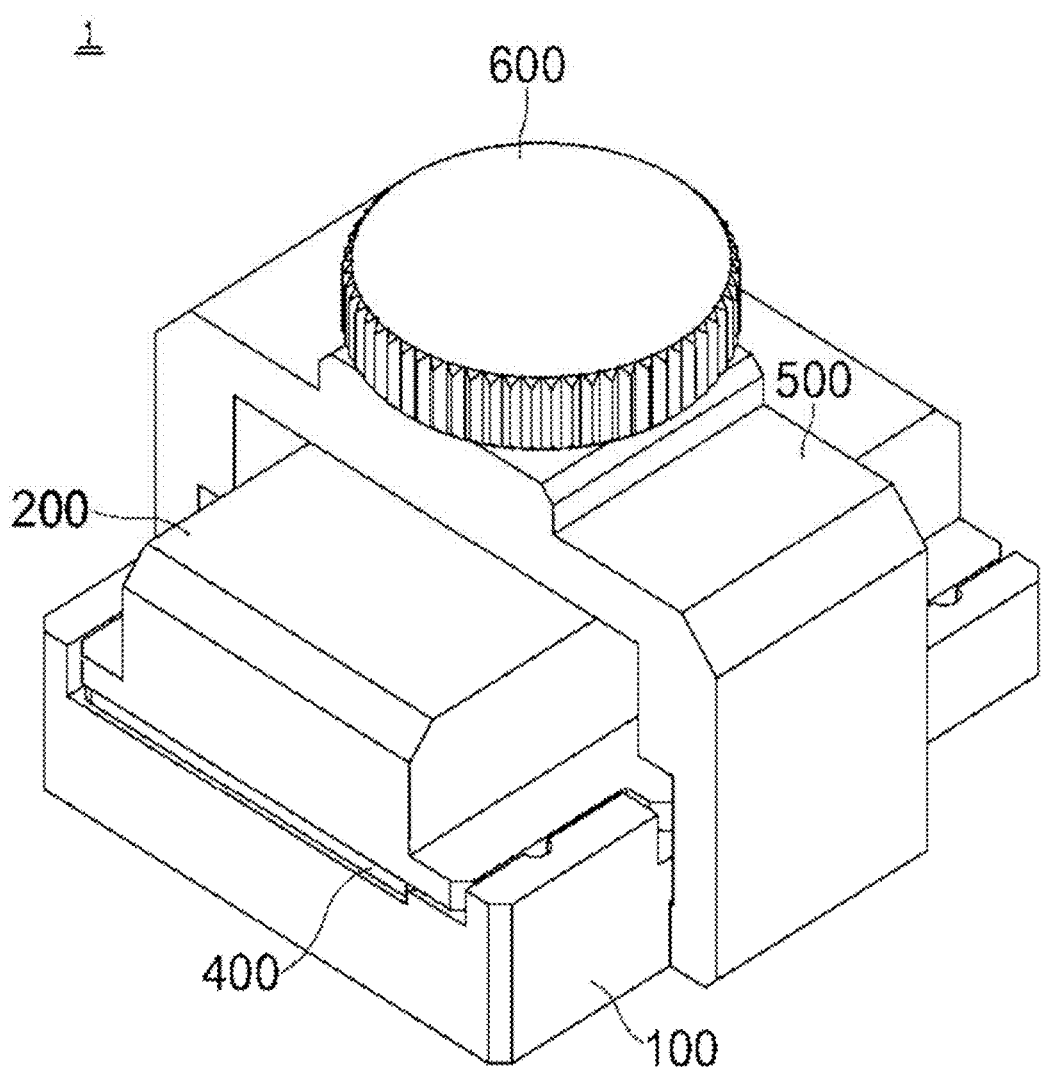

[Fig. 4]
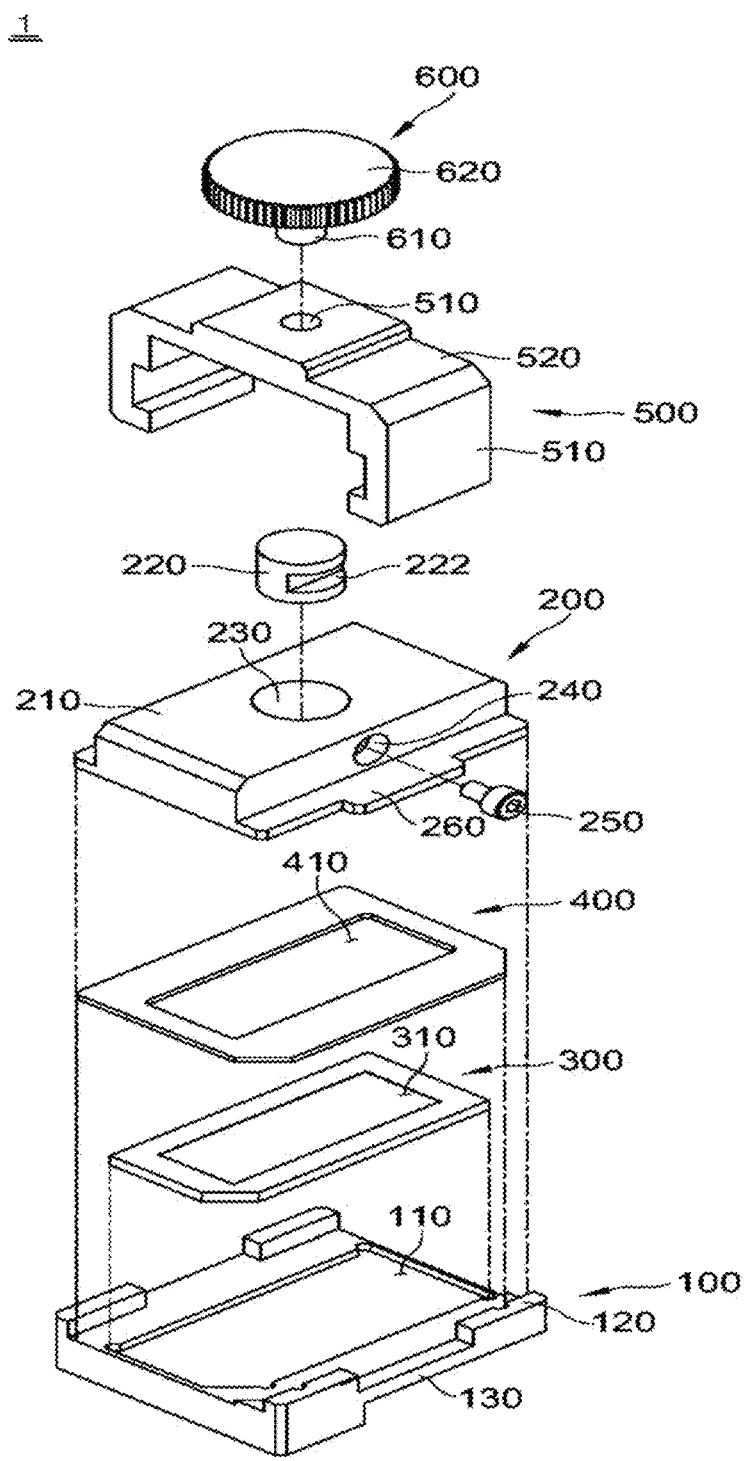

[Fig. 5]
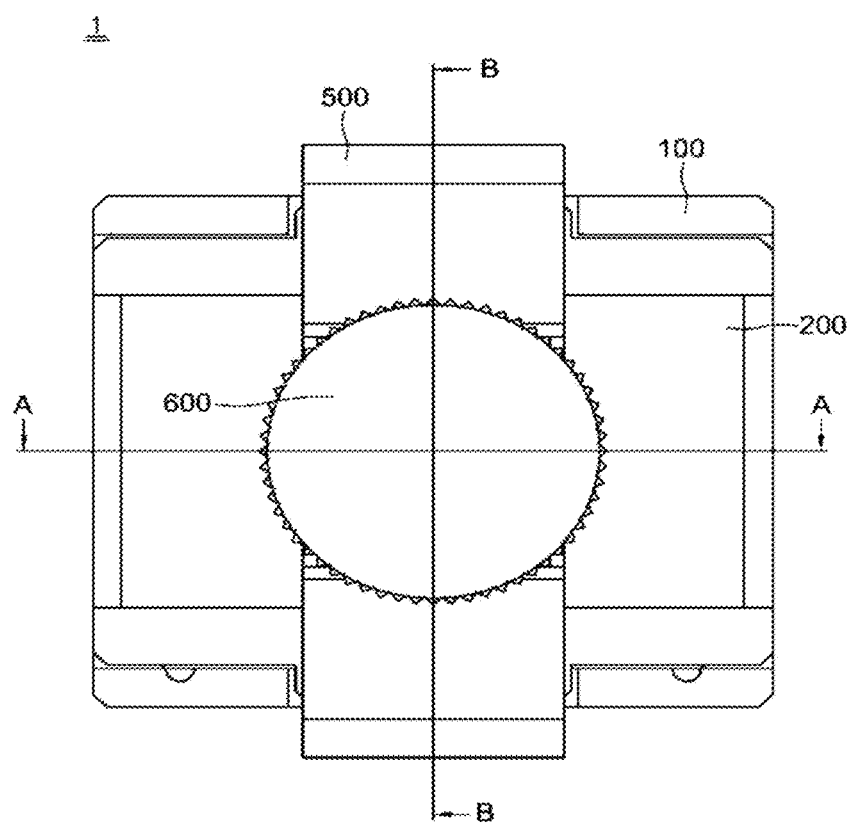

[Fig. 6]
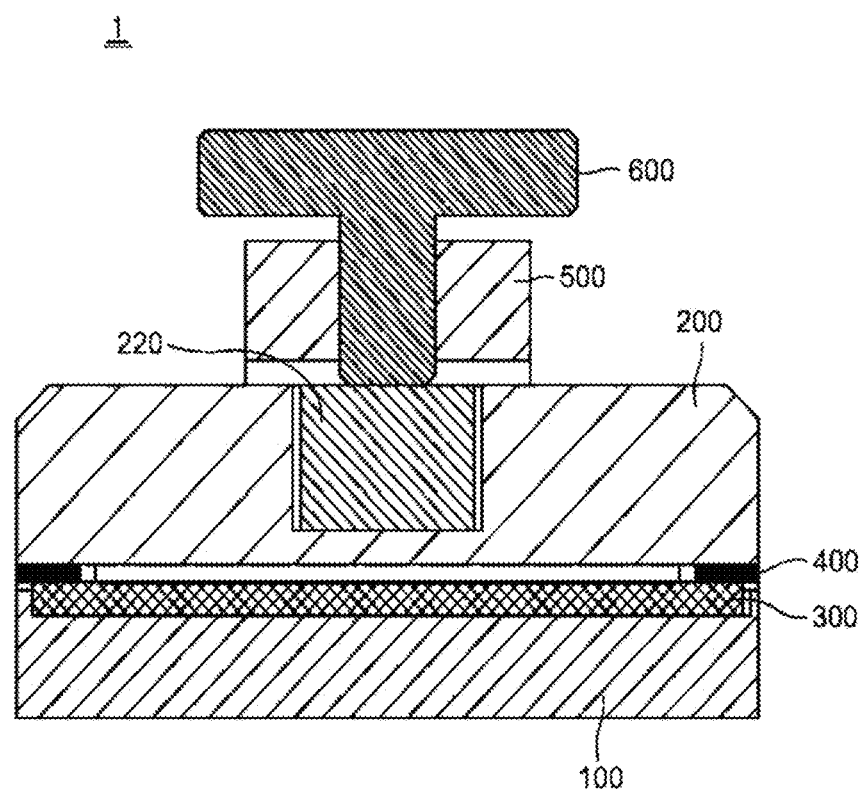

[Fig. 7]
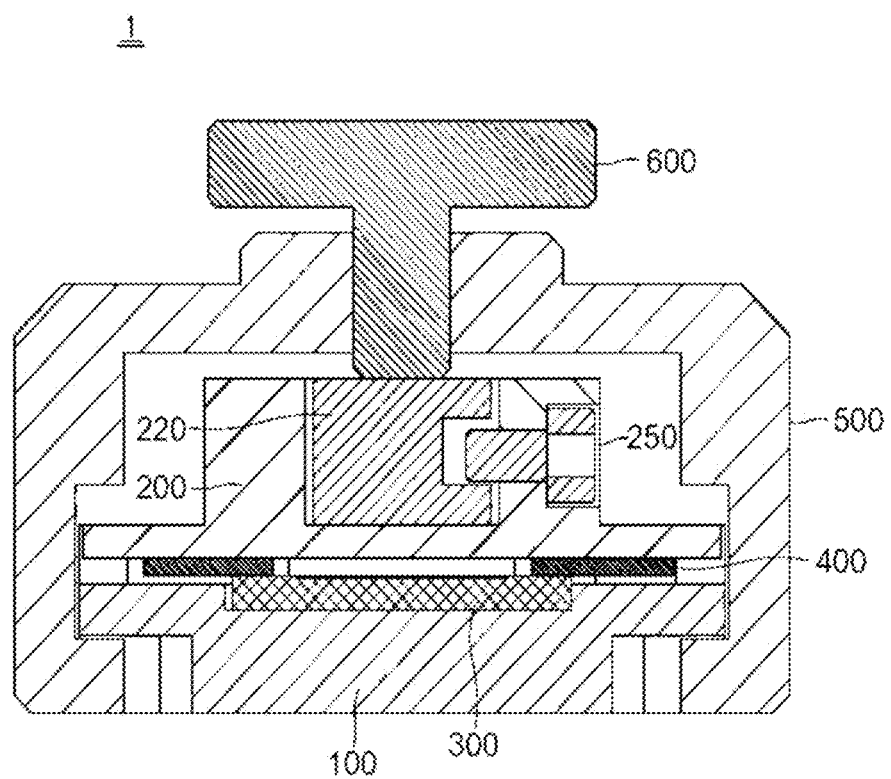

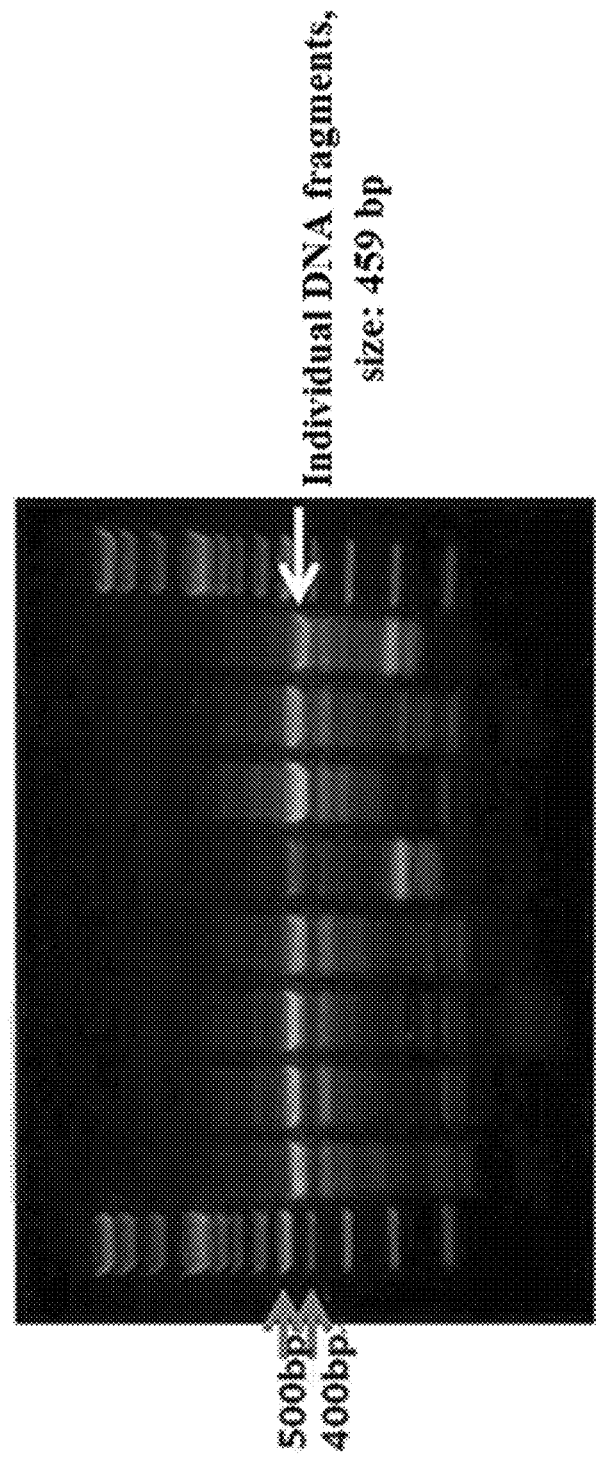
[Fig. 9]

[Fig. 10]

| Sample | Error free or not |
|---|---|
| F1_1 | Error free |
| F1_2 | Error free |
| F1_3 | Error free |
| F2_1 | Error free |
| F2_2 | Error free |
| F3_1 | Error free |
| F3_2 | Error free |
| F4_1 | Error free |

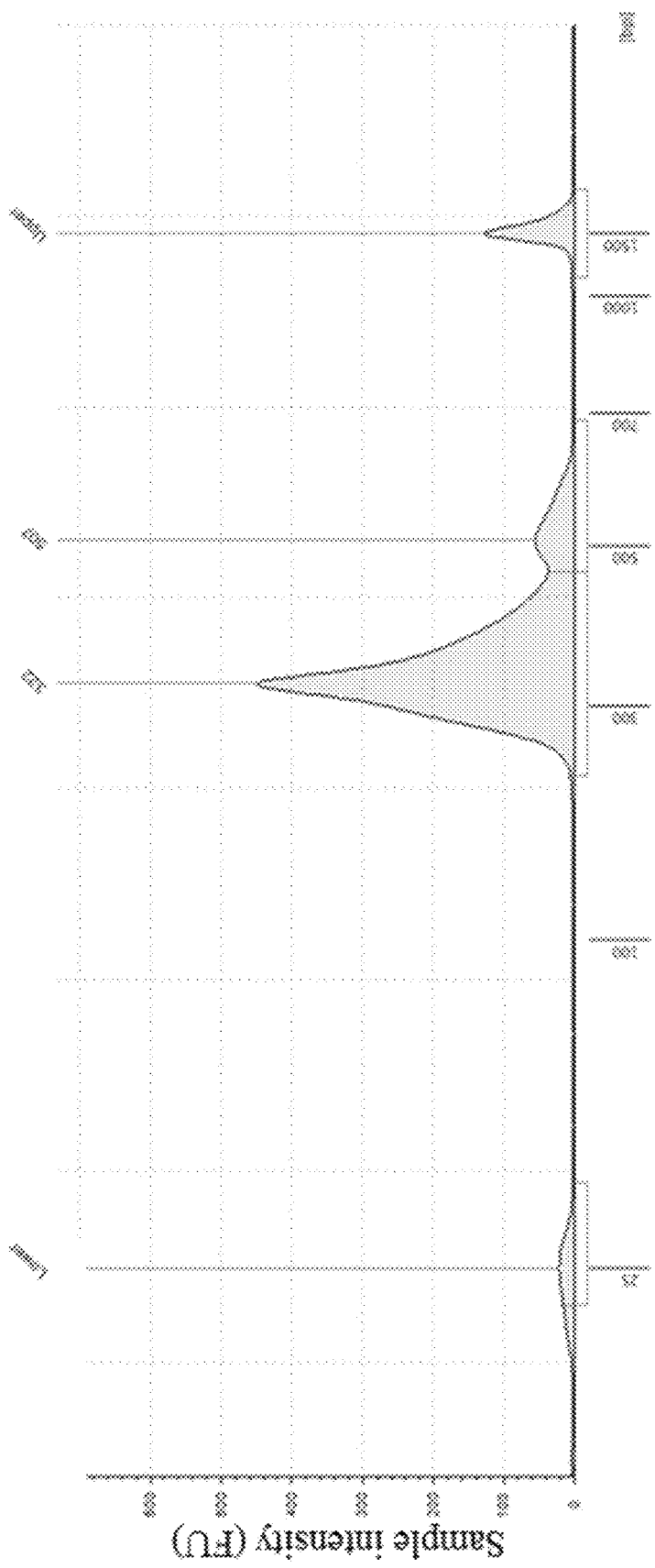

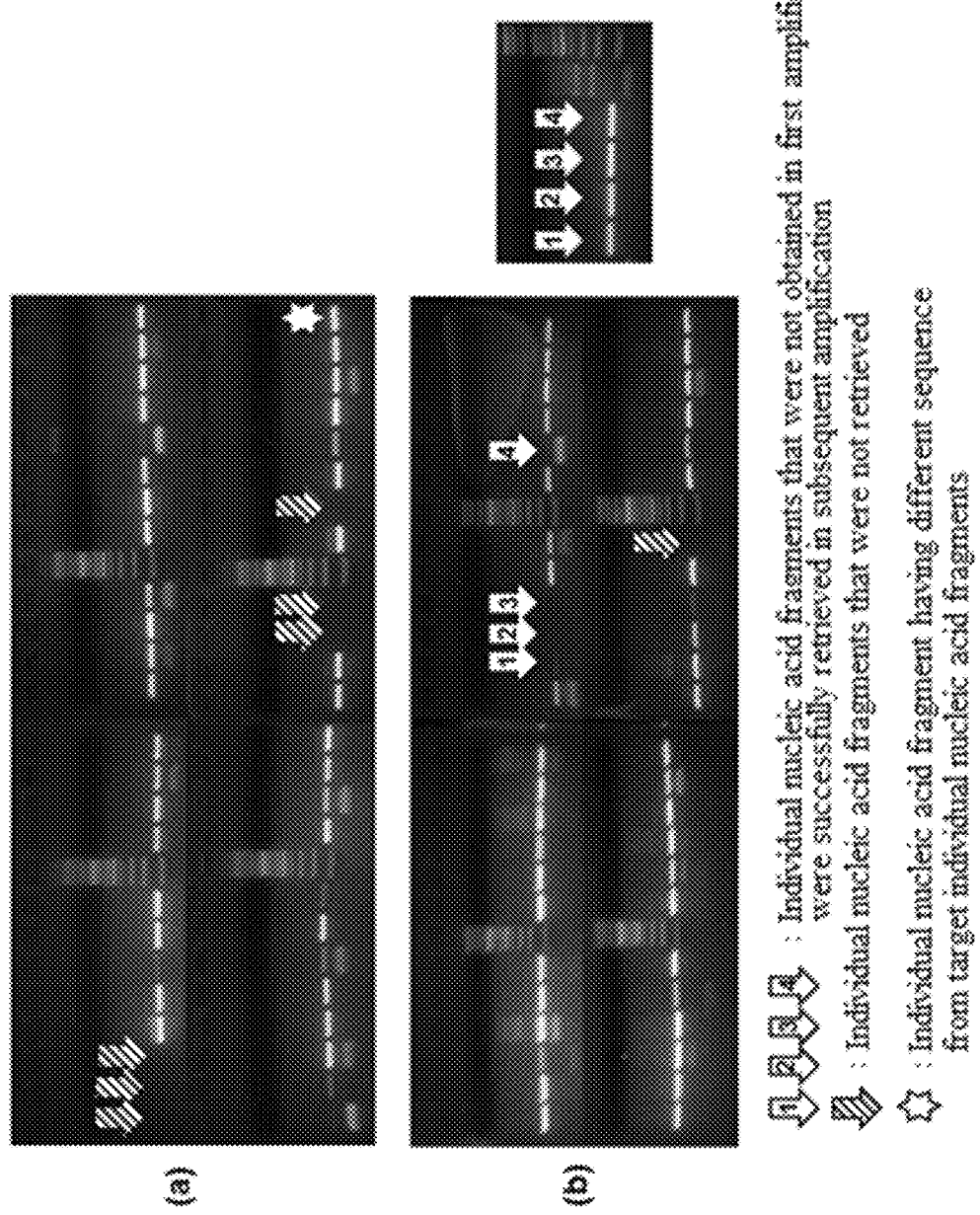

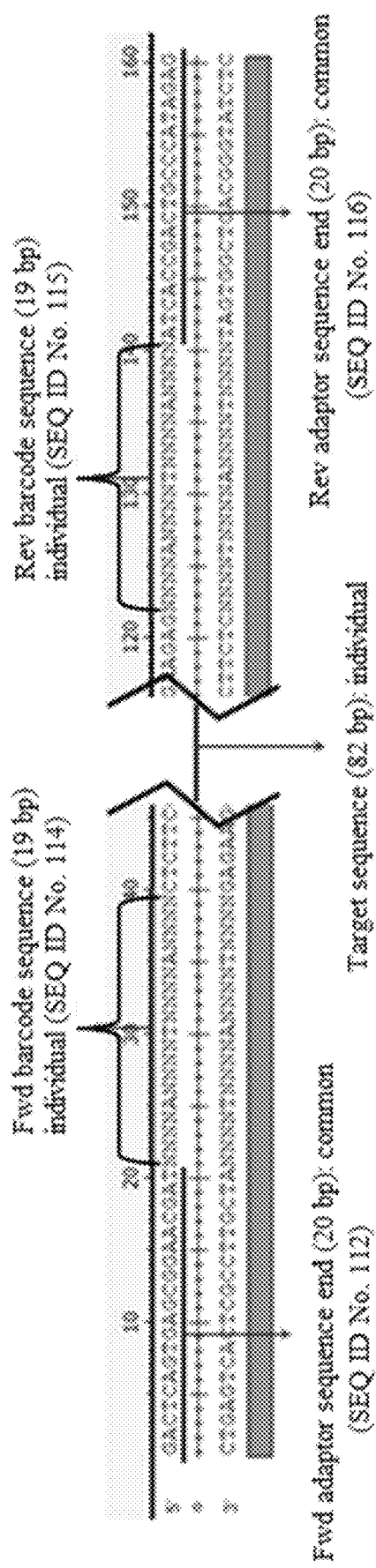
[Fig. 13]

[Fig. 14]
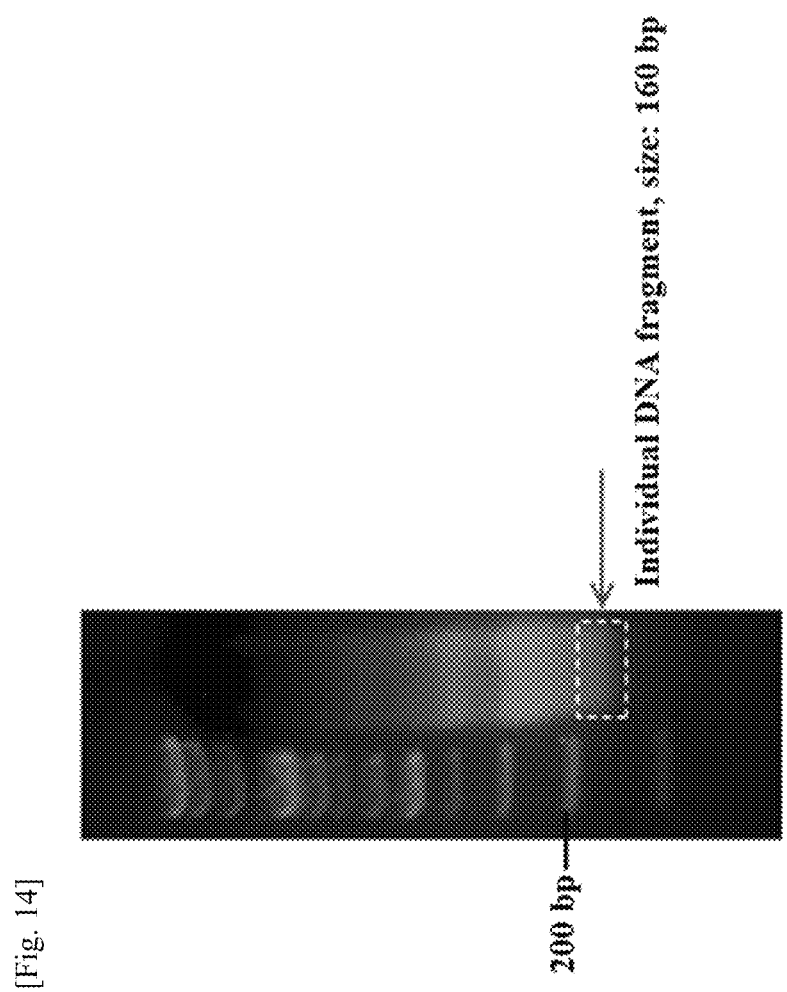

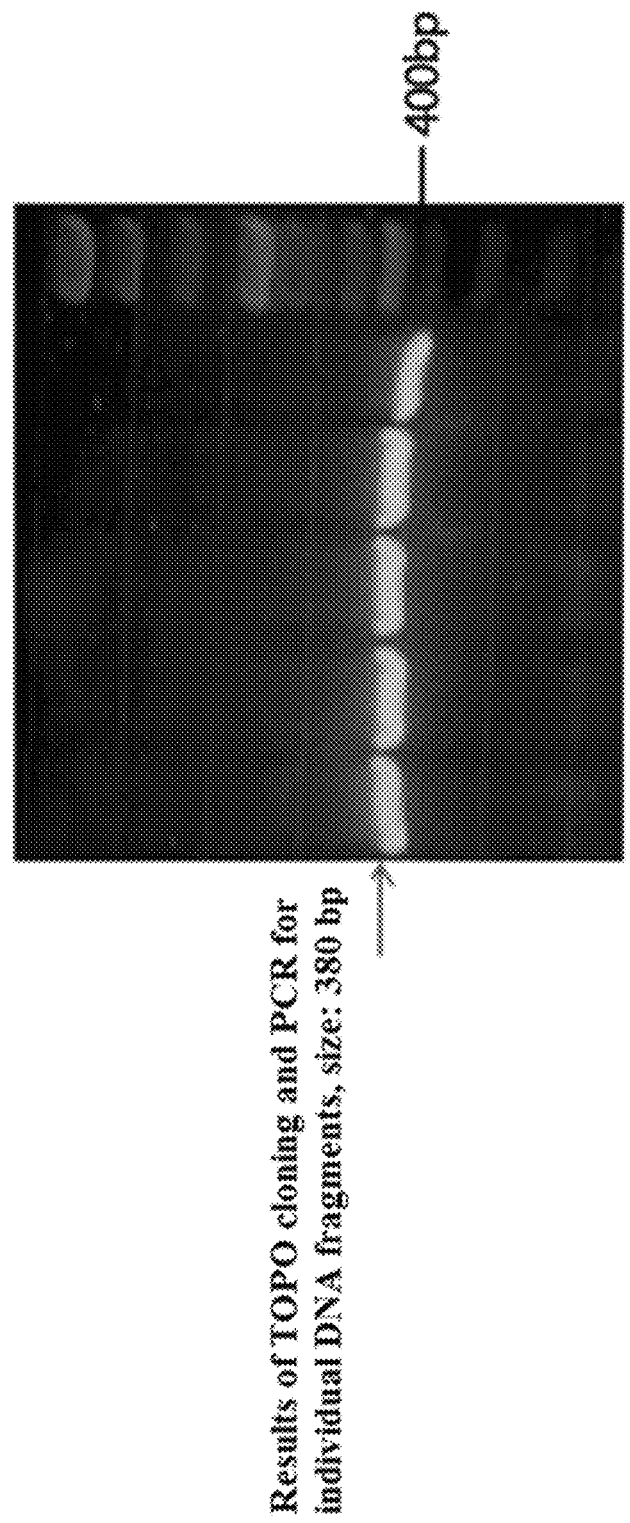

[Fig. 16]

| sample | Adaptor sequence end (common), Barcode sequence (individual), Target sequence (individual) |
|---|---|
| sample #1 (SEQ ID No. 117) | GACTCAGTGAGGGAAGGATGCTGACTGGTACGGAGGGTCTCTTCGCGGGGCGGTCCACG<br>GTCTCACTCTGCACGGCCTCGATCTTGTAGGGGATGTTGAGGGTGCCAGGGAAGAGTTGG<br>AATTGTGCCCAGTGTATCACGACTGCCATAGAG |
| sample #2 (SEQ ID No. 118) | GACTCAGTGAGGGAAGGATCGGCAACTATAAACATTGCTCTTCATGGAGCCTCCGCACG<br>TGGACGTTCTGGACGTGCAGGGTGACCTGCCAGCCCCGAGCCCCCAGGGGAGCCGGGAAGAGAAGC<br>ATGTGTGTCCATCAAATCACGACTGCCATAGAG |
| sample #3 (SEQ ID No. 119) | GACTCAGTGAGGGAAGGATGCTGACTGGTACGGAGGGTCTCTTCGCGGGGCGGTCCACG<br>GTCTCACTCTGCACGGCCTCGATCTTGTAGGGGATGTTGAGGGTGCCAGGGAAGAGTTGG<br>AATTGTGCCCAGTGTATCACGACTGCCATAGAG |
| sample #4 (SEQ ID No. 120) | GACTCAGTGAGGGAAGGATCTGGATGGTTCACCATGATCTCTTCGGAACTTGGCTCCAGCATG<br>GGCTGTGTAGGTGTCCCTGTCATCAACCTGCTCAGGCCAAATCAGCTACGAAGAGCTACAAC<br>AAGTTCTATTCTATCACGACTGCCATAGAG |
| sample #5 (SEQ ID No. 121) | GACTCAGTGAGGGAAGGATCGGCAACTATAAACATTGCTCTTCATGGAGCCTCCGCACG<br>TGGACGTTCTGGACGTGCAGGGTGACCTGCCAGCCCCGAGCCCCCAGGGGAGCCGGGAAGAGAAGC<br>ATGTGTGTCCATCAAATCACGACTGCCATAGAG |

METHODS FOR RETRIEVING SEQUENCE-VERIFIED NUCLEIC ACID FRAGMENTS AND APPARATUSES FOR AMPLIFYING SEQUENCE VERIFIED NUCLEIC ACID FRAGMENTS

CROSS REFERENCE TO PRIOR APPLICATIONS

This application is continuation-in-part application of PCT International Patent Application Nos. PCT/KR2014/005439 filed Jun. 19, 2014 which claims priority to Korean Patent Application No. 10-2013-0070660 filed Jun. 19, 2013, and PCT/KR2015/000828 filed Jan. 27, 2015 which claims priority to Korean Patent Application No. 10-2014-0010407 filed Jan. 28, 2014, which are all hereby incorporated by reference in their entirety.

TECHNICAL FIELD

The present disclosure relates to methods for retrieving sequence-verified nucleic acid fragments during sequencing and sealing chambers for implementing the methods.

BACKGROUND ART

With the recent advances in bioscience, high-throughput, highly parallel DNA synthesis and analysis technologies have also gained more importance. Since the beginning of the twentieth century, high-throughput, highly parallel DNA analysis has been driven by advances in next-generation sequencing technology. The development of new assays has greatly reduced the time required for analysis and increased the amount of analyzable data. Next-generation sequencing assays, such as Illumina, Roche-454, and Ion-Torrent-based sequencing assays, are currently in use. According to these assays, each target DNA library is attached to a solid and sequencing is performed based on chemical reactions at the site. With the recent remarkable development and growing application range of gene synthesis technologies, development of high-throughput, highly parallel gene synthesis technologies has been of increasing importance. An essential requirement for highly parallel gene synthesis is to synthesize error-free nucleic acid fragments in a cost effective manner. In conventional gene synthesis methods, chemically synthesized nucleic acid molecules are utilized for gene synthesis without further processing. However, since nucleic acid molecules are chemically synthesized in yields below 100%, error-free nucleic acid molecules and nucleic acid molecules containing synthesizing errors exist in the form of mixtures. Likewise, error-free genes and error-containing genes coexist in genes composed of chemically synthesized nucleic acid molecules. Thus, labor-intensive cloning and Sanger sequencing procedures are required for the selection of error-free genes.

Recent next-generation sequencing assays allow for cost-effective sequencing of millions of nucleic acid molecules at one time. Next-generation sequencing assays of nucleic acid fragments provide only information on the sequences of the nucleic acid fragments, and retrieval of the nucleic acid fragments after sequencing is very troublesome. Several methods for retrieving desired nucleic acid fragments after next-generation sequencing have recently been developed. According to the first method, information on each well of an analytical plate and information on the analyzed sequences are mapped after next-generation sequencing, beads attached with desired nucleic acid fragments remaining on the plate are picked, followed by amplification (High-fidelity gene synthesis by retrieval of sequence-verified DNA identified using high-throughput pyrosequencing, 2010 Nature Biotechnology, Mark Matzas et al.). According to the second method, organism-derived or artificially synthesized DNA libraries are tagged with barcode sequences, a portion of the DNA pool is analyzed by next-generation sequencing ('Shotgun DNA synthesis' for the high-throughput construction of large DNA molecules, 2012 Nucleic Acids Research, Kim et al., Accurate gene synthesis with tag-directed retrieval of sequence-verified DNA molecules, 2012, Schwartz J J et al.), and desired nucleic acid fragments are selectively amplified from the remaining DNA pool using primers including barcode sequences. These methods have an advantage in that sequence-verified nucleic acid fragments identified by next-generation sequencing can be selectively retrieved.

However, the first method requires the use of a costly system to directly retrieve sequence-verified oligonucleotide from a plate and is applied only to 454 sequencing platforms, resulting in poor versatility. The second method has many limitations in retrieving desired nucleic acid fragments using barcode sequences owing to a very large population of organism-derived or artificially synthesized DNA libraries. For example, when it is intended to synthesize hundreds of genes simultaneously, hundreds of millions to tens of billions of kinds of nucleic acid fragments are included in the pool irrespective of whether the nucleic acid fragments are error-free or not. Only one kind of desired individual nucleic acid fragment selected by an experimenter is difficult to selectively amplify from the pool due to the vast population of libraries and its retrieval yield is also low. And owing to the large population of the pool like synthesized DNA libraries, there could be plurality of nucleic acid fragments having similar barcode sequences each other. Therefore undesired nucleic acids having barcode sequences similar to the barcode sequences of the target nucleic acids are also retrieved.

PRIOR ART DOCUMENTS

Non-Patent Documents

1. Michael L. Metzker, Nature Reviews, Vol II. January 2010.
2. High-fidelity gene synthesis by retrieval of sequence-verified DNA identified using high-throughput pyrosequencing, 2010 Nature Biotechnology, Mark Matzas et al.
3. 'Shotgun DNA synthesis' for the high-throughput construction of large DNA molecules, 2012 Nucleic Acids Research, Kim et al.
4. Accurate gene synthesis with tag-directed retrieval of sequence-verified DNA molecules, 2012, Schwartz J J et al.

DETAILED DESCRIPTION OF THE INVENTION

Problems to be Solved by the Invention

One object of the present invention is to provide methods for easily retrieving desired individual nucleic acid fragments via replication of sequence-verified nucleic acid fragments from an entire pool of DNA libraries.

Another object of the present invention is to provide sealing chambers for retrieving sequence-verified nucleic acid fragments.

Means for Solving the Problems

According to one aspect of the present invention, there is provided a method for retrieving nucleic acid fragments, including providing reduced DNA libraries during sequencing, amplifying nucleic acid fragments from the reduced DNA libraries, and retrieving the amplified nucleic acid fragments.

According to a further aspect of the present invention, there is provided a method for retrieving nucleic acid fragments, including placing sequence-verified nucleic acid fragments after sequencing in an amplifier, amplifying the sequence-verified nucleic acid fragments, and retrieving the amplified nucleic acid fragments.

According to another aspect of the present invention, there is provided a method for retrieving nucleic acid fragments, including collecting single-stranded nucleic acid fragments separated during sequencing, amplifying the collected single-stranded nucleic acid fragments, and retrieving the amplified nucleic acid fragments.

According to another aspect of the present invention, there is provided a sealing chamber for amplifying nucleic acid fragments, including a base chamber adapted to receive a sequencing plate with nucleic acid fragments, an upper chamber detachably coupled to the base chamber and adapted to form a sealing structure as a whole when coupled to the base chamber, and an elastic sealing gasket arranged between the base chamber and the upper chamber wherein the base chamber is coupled to the upper chamber to create an internal space where a PCR solution for amplifying the nucleic acid fragments is accommodated and at least one of the base chamber and the upper chamber is made of a thermally conductive material.

According to yet another aspect of the present invention, there is provided a sealing chamber for amplifying nucleic acid fragments, including a base chamber formed with a receiving chamber, an upper chamber arranged on the base chamber, a reagent accommodating part received in the receiving chamber and having an accommodation space where a reagent for amplifying nucleic acid fragments is accommodated, an elastic gasket arranged between the base chamber and the upper chamber, a jig connected to the base chamber, extending above the upper chamber, and having an internally threaded hole formed in the upper portion thereof, and a pressurization part screwed into the threaded hole wherein the pressurization part includes an externally threaded portion and a head arranged on the threaded portion and pressurizes the upper chamber when it is displaced relative to the jig by turning of the head.

Effects of the Invention

According to the methods of the present invention, DNA libraries are reduced before amplification, resulting in a significant increase in the retrieval yield of desired nucleic acid fragments. When DNA libraries are very large in population, the complexity of the DNA libraries limits the retrieval yields of nucleic acid fragments therefrom. The methods of the present invention can reduce DNA libraries to reduce the complexity of the DNA libraries, achieving high retrieval yields of desired nucleic acid fragments. The methods of the present invention efficiently overcome the limitations of the conventional methods utilizing sequence-verified nucleic acid fragments to increase the availability of sequence-verified nucleic acid fragments.

The sealing chambers of the present invention are constructed such that an upper chamber is detachably coupled to a base chamber adapted to receive a sequencing plate with sequence-verified nucleic acid fragments and is adapted to form a sealing structure as a whole when coupled to the base chamber, the base chamber is coupled to the upper chamber to create an internal space where a PCR solution for amplifying the nucleic acid fragments is accommodated, and an elastic gasket is arranged between the base chamber and the upper chamber. Due to this construction, the sealing chambers can effectively prevent external impurities from entering reagents. In addition, the upper chamber is provided with a pressurization flap that can protect the upper chamber from damage and can be replaced with a new one, making it easy to maintain, repair, and manage the sealing chambers. Furthermore, the gasket, the upper chamber, and the base chamber are formed with irregularities that can increase the penetration paths of impurities to effectively block the penetration of impurities.

BRIEF DESCRIPTION OF THE DRAWINGS

FIG. 1 is a flow chart of a method for retrieving sequence-verified nucleic acid fragments after sequencing.

FIG. 2 shows the states of a sequencing plate in a sealing chamber according to one embodiment of the present invention before and after sealing.

FIG. 3 is a perspective view of a sealing chamber according to one embodiment of the present invention.

FIG. 4 is an exploded view of a sealing chamber according to one embodiment of the present invention.

FIG. 5 is a plan view of a sealing chamber according to one embodiment of the present invention.

FIG. 6 is a cross-sectional view taken along line A-A of FIG. 5.

FIG. 7 is a cross-sectional view taken along line B-B of FIG. 5.

FIG. 9 shows individual amplification products of retrieved sequence-verified nucleic acid fragments after sequencing with primers for selective amplification.

FIG. 10 shows the results of Sanger sequencing for selectively amplified individual nucleic acid fragments.

FIG. 11 shows the results of assay with Agilent TapeStation for retrieved products of sequence-verified nucleic acid fragments after sequencing.

FIG. 12 compares the retrieval of individual nucleic acid fragments from DNA libraries replicated in Illumina sequencing platforms with the retrieval of individual nucleic acid fragments from unreplicated DNA libraries.

FIG. 13 shows the construction of a DNA library used in Example 6.

FIG. 14 shows the results obtained when a solution of collected nucleic acid fragments separated from sequencing beads was purified and the nucleic acid fragments were amplified in Example 8.

FIG. 15 shows the results of TOPO cloning and PCR for individual DNA fragments separated from amplified nucleic acid libraries in Example 8.

FIG. 16 is a table comparing the sequences of individual DNA fragments separated through TOPO cloning and PCR and verified by Sanger sequencing with the contents of original DNA libraries in Example 8.

MODE FOR CARRYING OUT THE INVENTION

Figure 8:
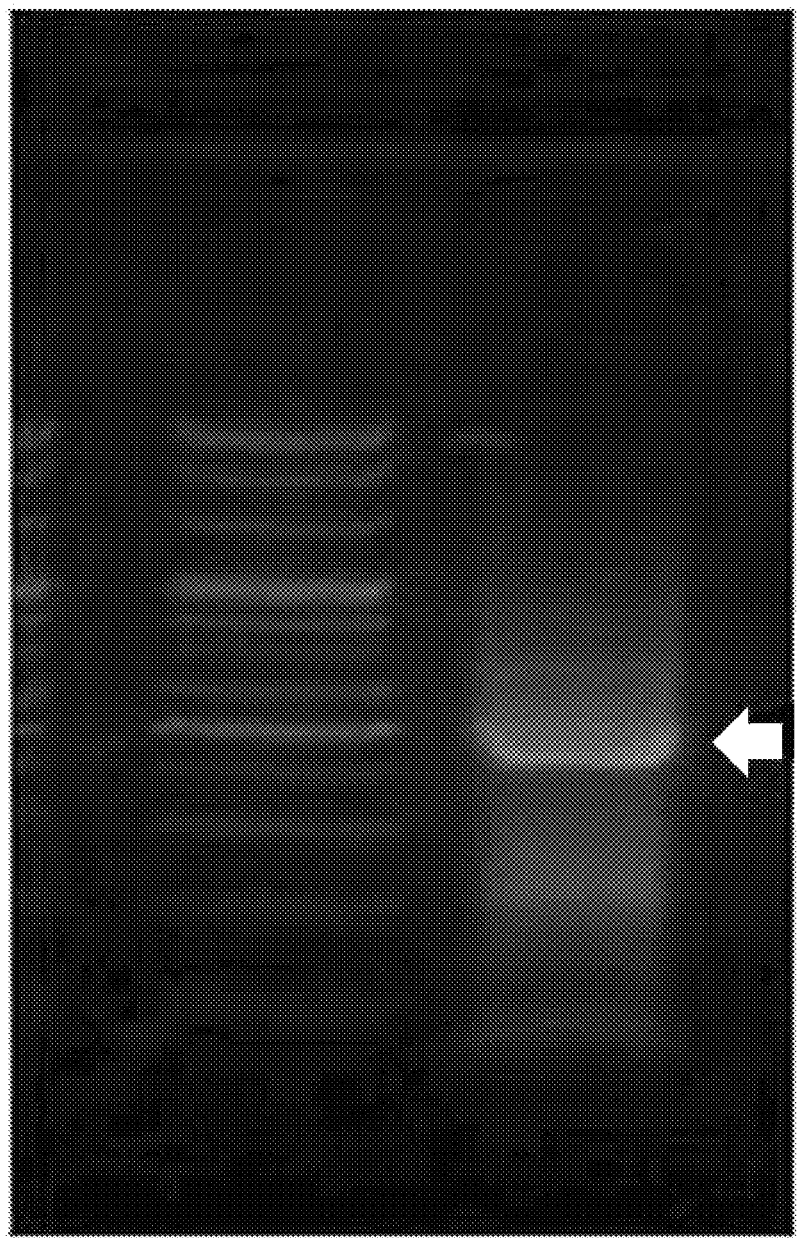
FIG. 8 shows retrieved sequence-verified nucleic acid fragments after sequencing.

Various embodiments of the present invention will now be described in more detail. These embodiments are provided so that this disclosure will fully convey the scope of the disclosure to those skilled in the art. Accordingly, the present invention may be embodied in many different forms and should not be construed as limited to the exemplary embodiments set forth herein.

As a result of intensive research to overcome the limitations of the method using bead picking or barcode sequences to retrieve nucleic acid fragments, the present inventors have succeeded in developing methods and apparatuses for retrieving all nucleic acid fragments analyzed by next-generation sequencing without loss by effectively reducing DNA libraries to mitigate limitations arising from the population of the DNA libraries.

According to one aspect of the present invention, there is provided a method for retrieving nucleic acid fragments, including providing reduced DNA libraries during sequencing, amplifying nucleic acid fragments from the reduced DNA libraries, and retrieving the amplified nucleic acid fragments.

According to a further aspect of the present invention, there is provided a method for retrieving nucleic acid fragments, including placing sequence-verified nucleic acid fragments after sequencing in an amplifier, amplifying the sequence-verified nucleic acid fragments, and retrieving the amplified nucleic acid fragments.

According to another aspect of the present invention, there is provided a method for retrieving nucleic acid fragments, including collecting single-stranded nucleic acid fragments separated during sequencing, amplifying the collected single-stranded nucleic acid fragments, and retrieving the amplified nucleic acid fragments.

In one embodiment, the method may further include attaching adaptor sequences to the nucleic acid fragments before sequencing, separating the adaptor-attached nucleic acid fragments into single strands, and sequencing the adaptor-attached single-stranded nucleic acid fragments, prior to placing the sequence-verified nucleic acid fragments in an amplifier.

The sequencing may be performed in such a manner to synthesize nucleic acid fragments. The synthesis of nucleic acid fragments may be performed by Sanger sequencing or highly parallel sequencing (Michael L. Metzker, Nature Reviews, Vol. II, 2010 January, 'Sequencing technologies—the next generation'). Herein, the highly parallel sequencing may be pyrosequencing chemistry, bridge amplification, next-generation sequencing, third-generation sequencing, next-next-generation sequencing or semiconductor sequencing but is not limited thereto.

When the nucleic acid fragments before sequencing are longer than nucleic acid fragments proposed in next-generation sequencing assays, they may be fragmented, for example, by digestion with restriction enzymes or physical shearing. Meanwhile, when the nucleic acid fragments before sequencing are shorter, they may be extended, for example, by assembly or ligation.

The amplifier may be a sealed sequencing plate where the nucleic acid fragments have been sequenced. As used herein, the term "sequencing plate" refers to a plate on which DNA libraries are fixed such that the DNA can be sequenced using a sequencer and may have an internal space in which the constituent nucleic acid fragments of the DNA libraries are fixed and an inlet in communication with the internal space. The DNA libraries are fixed in such a manner that beads attached with the DNA libraries are placed in wells in the form of lattices or the DNA libraries are directly attached to the inner surface of the plate. However, there is no limitation on the method for fixing the DNA libraries. A reagent necessary for reactions may be injected into the plate through the inlet. Sequencing and amplification reactions for retrieving the nucleic acid fragments may occur in the internal space of the plate. Examples of commercially available products for the sequencing plate include, but are not limited to, Flow cell (Illumina), Ion PI™ Chip (Life Technology), and PicoTiterPlate (GS Junior Titanium).

A reagent for amplification is injected into the sequencing plate including the sequence-verified nucleic acid fragments through the inlet, and the inlet is then closed. The sealed sequencing plate can be used as an amplifier for amplifying the nucleic acid fragments. Since the inlet of the sequencing plate containing the sequence-verified nucleic acid fragments is closed, the sequencing plate can be sealed in a state after completion of the sequence verification. For this sealing, the sequencing plate can be directly sealed with a sealing film made of a durable material, a tape or an adhesive, such as a gum. However, there is no limitation on how to seal the sequencing plate. One embodiment associated with the sealing of the sequencing plate is shown in FIG. 2. Referring to FIG. 2, the inlet of the sequencing plate (Illumina) is closed with a tape to seal the sequencing plate containing the sequence-verified nucleic acid fragments. As a result of this sealing, an internal space is formed in the sequencing plate to accommodate a reagent for the amplification of the nucleic acid fragments.

The amplifier may be a sealing chamber in which a reagent is accommodated and sealed. The sealing chamber for amplifying the nucleic acid fragments may include a base chamber adapted to receive the sequencing plate with the nucleic acid fragments, an upper chamber detachably coupled to the base chamber and adapted to form a sealing structure as a whole when coupled to the base chamber, and an elastic sealing gasket arranged between the base chamber and the upper chamber. The base chamber is coupled to the upper chamber to create an internal space where a PCR solution for amplifying the nucleic acid fragments is accommodated. At least one of the base chamber and the upper chamber is made of a thermally conductive material. Thereafter, when the sealing chamber is immersed in a water bath, this material facilitates control over the temperature of the internal PCR solution by the temperature control of the water bath.

One embodiment of the sealing chamber is illustrated in FIG. 3. Referring to FIG. 3, the sealing chamber 1 includes a base chamber 100, an upper chamber 200, a reagent accommodating part 300, a gasket 400, a jig 500, and a pressurization part 600. However, the sealing chamber 1 is not limited to the structure illustrated in FIG. 3.

When it is intended to place sequence-verified nucleic acid fragments in an amplifier, a sequencing plate containing the sequence-verified nucleic acid fragments in a state after completion of the sequence verification may be placed in the amplifier. That is, the collected plate for next-generation sequencing can be mounted and sealed in the sealing chamber. The plate containing all sequence-verified nucleic acid fragments is placed in the amplifier without tearing off a portion of the sequencing plate or separating the sequence-verified nucleic acid fragments from the plate.

In one embodiment of the present invention, the single-stranded nucleic acid fragments separated during sequencing may be collected.

According to a further embodiment of the present invention, there is provided a method for retrieving nucleic acid fragments based on the reduction of libraries of nucleic acid fragments by highly parallel sequencing. The method may include (a) preparing sequencing beads with amplified double-stranded DNA libraries, (b) collecting single-stranded nucleic acid fragments separated from the sequencing beads to provide reduced DNA libraries, (c) amplifying the collected single-stranded nucleic acid fragments, and (d) retrieving the amplified nucleic acid fragments.

In a preferred embodiment, the method may optionally further include (e) acquiring desired nucleic acid fragments among the retrieved nucleic acid fragments.

According to another embodiment of the present invention, there is provided a method for retrieving nucleic acid fragments, including (a) providing DNA libraries, (b) attaching the DNA libraries to beads for next-generation sequencing, (c) amplifying the DNA libraries attached with the beads, (d) separating the nucleic acid fragments amplified on the beads into single strands, (e) collecting and purifying a solution of the single-stranded nucleic acid fragments separated from the beads, (f) amplifying the collected nucleic acid fragments, and (g) acquiring desired nucleic acid fragments among the retrieved nucleic acid fragments.

In the case where the amplified nucleic acid fragments are tagged with specific barcode sequences, the desired nucleic acid fragments may be acquired using sequences having a homology to the barcode sequences.

The single-stranded nucleic acid fragments separated during sequencing may be those separated from solid supports, such as sequencing beads, sequencing plates, and sequencing clonal clusters. The solid supports may be provided with DNA libraries. For highly parallel sequencing, amplified double-stranded nucleic acid fragments may be attached with the solid supports. According to one embodiment of the present invention, the beads are separated into single-stranded nucleic acid fragments for sequencing and are injected into a sequencing plate. At this time, opposite single-stranded nucleic acid fragments unattached with the beads can be collected separately. According to conventional methods, single-stranded nucleic acid fragments immobilized on solid supports are subjected to sequencing and free single-stranded nucleic acid fragments separated from the solid supports are wasted. Since the free single-stranded nucleic acid fragments have sequences complementary to the sequence-verified nucleic acid fragments, amplification and retrieval of the free single-stranded nucleic acid fragments can bring about the same results as the retrieval of the sequence-verified nucleic acid fragments. The number of the collected single-stranded nucleic acid fragments is smaller than that of the nucleic acid fragments in the original DNA libraries.

The single-stranded nucleic acid fragments separated from the sequencing beads are collected to provide reduced DNA libraries. This process can be explained as follows. For example, when DNA libraries acquired using 90 k microchip oligos are analyzed by Ion-Torrent sequencing, adaptor sequences necessary for sequencing are connected to about $2-5\times10^{14}$ nucleic acid fragments, the connected attached nucleic acid fragments are mixed with about $5\times10^8$ sequencing beads, followed by emulsion PCR. As a result of the PCR, only one kind of nucleic acid fragment is amplified on one kind of bead to form double-stranded nucleic acids. Thereafter, when nucleic acid fragments having different adaptor sequences at both ends are selectively separated for sequencing through enrichment, half of the nucleic acid fragments (about $2.5\times10^8$) remain. The beads are separated into single-stranded nucleic acid fragments for sequencing and are injected into a sequencing chip. At this time, opposite single-stranded nucleic acid fragments unattached with the beads can be collected separately. The number of the collected single-stranded nucleic acids having undergone amplification and enrichment on the sequencing beads is about $2.5\times10^8$, which is smaller than that of the nucleic acid fragments (ca. $2-5\times10^{14}$) in the original DNA libraries. The number of pieces of information of the nucleic acid fragments obtained by sequencing is about $1-2\times10^8$. Since the nucleic acid fragments having the information are all included in the reduced libraries, the use of the reduced libraries rather than the original libraries leads to an increase in retrieval yield.

As another example, the reduction of the DNA libraries by collecting the single-stranded nucleic acid fragments separated from the sequencing beads may be analyzed using Roche-454 GS Junior. This process is explained as follows. The concentration of the original DNA libraries (ca. $2-5\times10^{14}$) acquired using microchip oligos is measured and the number of the molecules is calculated for dilution. At this time, emulsion PCR is conducted by reacting $5-20\times10^6$ nucleic acid fragments with a larger number of sequencing beads. Thereafter, some ($2\times10^5$-$5\times10^5$, more broadly $1\times10^5$-$3\times10^6$) of the sequencing beads attached with the nucleic acid fragments amplified by emulsion PCR are collected and the single-stranded nucleic acid fragments unattached with the beads are collected. As a result, libraries ($2-5\times10^5$) whose nucleic acid fragments are smaller in number than those of the original DNA libraries (ca. $2\times10^{14}$) can be obtained. The number of the libraries can also be arbitrarily restricted by limiting the number of the sequencing beads. The number of pieces of information of the nucleic acid fragments obtained by sequencing is about $5\times10^4$-$1\times10^5$. Since the nucleic acid fragments having the information are all included in the reduced libraries, the use of the reduced libraries rather than the original libraries leads to an increase in retrieval yield.

The method may further include purifying a solution of the collected single-stranded nucleic acids of the reduced libraries to retrieve pure nucleic acid fragments only.

Next, the sequence-verified nucleic acid fragments or the collected nucleic acid fragments separated during sequencing are amplified.

The method may further include injecting a DNA polymerase, dNTPs, a primer, a buffer, and/or a PCR solution into the nucleic acid fragments to amplify the nucleic acid fragments. The DNA polymerase is not limited but may be, for example, Taq or Pfu polymerase.

Next, the amplified nucleic acid fragments are retrieved. For example, the amplified nucleic acid fragments, together with the PCR solution, may be retrieved using a suitable device, such as a pipette. As another example, only the amplified nucleic acid fragments may be retrieved by electrophoresis of the PCR solution on an agarose gel and selective purification of bands corresponding to the sizes of the nucleic acid fragments included in the libraries. The use of this method enables the retrieval of all sequence-verified nucleic acid fragments without loss.

The desired nucleic acid fragments may be acquired by any conventional process. For example, a commercially available kit for the retrieval of nucleic acid fragments may be directly applied or a method using the kit may be applied to the acquisition of the desired nucleic acid fragments. In the case where the amplified nucleic acid fragments are attached with beads or tagged with particular barcode sequences, the desired nucleic acid fragments may be acquired by collecting the beads or using sequences having a homology to the barcode sequences.

The nucleic acid fragments may be amplified or extended using an oven, a water bath or a temperature-controllable instrument, for example, a PCR instrument.

The method may further include attaching adaptor sequences to the nucleic acid fragments before sequencing and sequencing the adaptor-attached nucleic acid fragments prior to placing the sequence-verified nucleic acid fragments in an amplifier.

The adaptor sequences may be attached by PCR assembly or ligation. If needed, 15-30 bp long barcode sequences may be added when the adaptor sequences are attached.

The method may further include collecting the sequencing plate after sequencing. Washing and bleaching of the sequencing plate are not required. Washing and bleaching are the final steps in next-generation sequencing.

According to a further embodiment of the present invention, there is provided a method for retrieving nucleic acid fragments based on the reduction of libraries of nucleic acid fragments by highly parallel sequencing. Specifically, the method may include (a) preparing a sequencing plate with DNA libraries, (b) subjecting the DNA libraries to highly parallel sequencing to provide reduced libraries of sequence-verified nucleic acid fragments, (c) placing the sequencing plate with all sequence-verified nucleic acid fragments in an amplifier, (d) amplifying all nucleic acid fragments placed in the amplifier, and (e) retrieving the amplified nucleic acid fragments.

In a preferred embodiment, the method may optionally further include (f) acquiring desired nucleic acid fragments among the retrieved nucleic acid fragments.

A process for reducing the DNA libraries by highly parallel sequencing can be explained as follows. For example, DNA libraries including hundreds of millions to tens of billions of kinds of nucleic acid fragments may be analyzed using Roche-454 GS Junior. The process is briefly explained as follows. First, the concentration of the original DNA libraries is measured during sequencing preparation and the number of the molecules is calculated for dilution. At this time, emulsion PCR is conducted by reacting $5\text{-}20 \times 10^6$ nucleic acid fragments with $10^7$ sequencing beads. Thereafter, the sequencing beads attached with the nucleic acid fragments amplified by emulsion PCR, are collected, washed, enriched, injected into a sequencing plate, followed by sequencing. About 50 to 100 thousands of sequencing reads are obtained after successful sequencing of the nucleic acid fragments. That is, the number of the nucleic acid fragments obtained after sequencing is smaller than the number of the nucleic acid fragments in the original DNA libraries. For example, DNA libraries including hundreds of millions to tens of billions of kinds of nucleic acid fragments may be analyzed using Ion-Torrent Proton. In this case, adaptor sequences necessary for sequencing are connected to about $7\text{-}10 \times 10^{11}$ nucleic acid fragments, the connected nucleic acid fragments are mixed with the same number of sequencing beads, followed by emulsion PCR. As a result of the PCR, only one kind of nucleic acid fragment is amplified on one kind of bead to form double-stranded nucleic acids. Thereafter, when nucleic acid fragments having different adaptor sequences at both ends are selectively separated for sequencing through enrichment, half of the nucleic acid fragments (about $3\text{-}5 \times 10^{11}$) remain. About 60 to 80 millions of sequencing reads are obtained after successful sequencing. That is, the number of the nucleic acid fragments obtained after sequencing is smaller than the number of the nucleic acid fragments in the original DNA libraries.

According to the methods of the present invention, only the DNA libraries included in the sequencing plate are analyzed by next-generation sequencing. As a result, the proportion of the sequenced DNA libraries in all DNA libraries can be effectively reduced to the number of the reads for next-generation sequencing. After completion of the sequencing, the sequencing plate is placed in the sealing chamber and the reduced DNA libraries are amplified. The amplified DNA libraries can be retrieved from the sequencing plate. The presence of barcode sequences in the DNA libraries ensures high retrieval yields of desired nucleic acid fragments from the reduced DNA libraries.

According to another embodiment of the present invention, there is provided a method for retrieving nucleic acid fragments based on the use of the sequencing plate where the nucleic acid fragments have been sequenced, avoiding the use of a separate sealing chamber. The method may include (a) preparing a sequencing plate with DNA libraries, (b) sequencing nucleic acid fragments of the DNA libraries, (c) injecting a reagent for amplification into the sequencing plate where the nucleic acid fragments have been sequenced, (d) sealing the sequencing plate, (e) amplifying all nucleic acid fragments placed in the sealed sequencing plate, and (f) retrieving the amplified nucleic acid fragments.

Hereinafter, a sealing chamber according to a preferred embodiment of the present invention will be explained with reference to the accompanying drawings. This embodiment is not intended to limit the present invention.

Spatially relative terms, such as "lower," "upper" and the like, may be used herein for ease of description to describe the relationship of one member or element to another member(s) or element(s) as illustrated in the figures. It will be understood that the spatially relative terms are intended to encompass different orientations of the device in use or operation, in addition to the orientation depicted in the figures. For example, if the orientation of the member in the figures is altered to change the point of view, elements described as "side" relative to other elements would then be oriented "front" relative to the other elements. Thus, the exemplary term "side" can encompass both front and rear orientations. The member may be otherwise oriented and the spatially relative descriptors used herein interpreted accordingly.

In the drawings, the thickness or size of each member is exaggerated, omitted, or schematically illustrated for convenience in description and clarity. Also, the size or area of each constituent element does not entirely reflect the actual size thereof.

FIG. 3 is a perspective view of a sealing chamber according to one embodiment of the present invention, FIG. 4 is an exploded view of the sealing chamber, FIG. 5 is a plan view of the sealing chamber, FIG. 6 is a cross-sectional view taken along line A-A of FIG. 5, and FIG. 7 is a cross-sectional view taken along line B-B of FIG. 5.

Referring to FIGS. 3 and 4, the sealing chamber 1 includes a base chamber 100, an upper chamber 200, a reagent accommodating part 300, a gasket 400, a jig 500, and a pressurization part 600.

The base chamber 100 is formed with a receiving chamber 110 in which the reagent accommodating part 300 can be received and arranged. For example, the receiving chamber 110 may be a depressed portion formed on the upper surface of the base chamber 100. The receiving chamber 110 may have a shape corresponding to the contour of the reagent accommodating part 300, which will be described below. For example, each of the reagent accommodating part 300 and the receiving chamber 110 may be constructed to have a substantially rectangular shape whose one corner is chamfered, as illustrated in FIG. 4. However, there is no limitation on the shape.

The base chamber 100 may be made of a metal material, such as stainless steel, such that it can be protected from deformation and damage even under severe conditions, such as high pressure and high temperature conditions. However, there is no limitation on the material for the base chamber 100. Preferably, the base chamber 100 has guide portions 120 formed on the upper surface thereof to appropriately arrange and fixedly position the gasket 400 and the upper chamber 200, which will be described below. For example, the guide portions 120 may be guide protrusions formed at the corners of the base chamber 100.

The upper chamber 200 is arranged on the base chamber 100 and is in the form of a cover that covers the upper side of the reagent accommodating part 300, which will be described above. The upper chamber 200 may also be made of a metal material, such as stainless steel, such that it can be protected from deformation and damage even under severe conditions, such as high pressure and high temperature conditions. However, there is no limitation on the material for the upper chamber 200.

The reagent accommodating part 300 is designed to receive a reagent therein. For example, the reagent accommodating part 300 may be in the form of a plate-like member having an accommodation space 310. The accommodation space 310 may be in the form of a depressed portion in which a reagent is placed or a hole in which a reagent-containing member (e.g., a glass container) is accommodated. However, there is no limitation on the form of the accommodation space 310. As described above, it is preferred that the reagent accommodating part 300 has a contour corresponding to the shape of the receiving chamber 110. However, there is no limitation on the contour of the reagent accommodating part 300.

Preferably, the accommodation space 310 of the reagent accommodating part 300 varies in volume and shape. For example, the accommodation space 310 of the reagent accommodating part 300 may have a small volume when a very small amount of a reagent is necessary for an experiment. When it is desired to compare changes of various reagents under the same experimental conditions, a plurality of reagent accommodating parts 300 may be formed in the accommodation space 310. However, there is no limitation on the volume and shape of the accommodation spaces 310. Thus, even in the case where various experiments are conducted on reagents accommodated in the reagent accommodating part 300, the reagent accommodating part 300 may be appropriately replaced to conduct the experiments without the need to replace the sealing chamber 1 per se or the other members thereof, leading to improved convenience for users.

The reagent accommodating part 300 is received in the receiving chamber 110 of the base chamber 100. Due to this construction, the sealing chamber 1 may have a dual housing structure. That is, a reagent is accommodated in the reagent accommodating part 300 received in the receiving chamber 110 of the base chamber 100, accomplishing a dual housing structure of the sealing chamber 1.

The gasket 400 is arranged between the base chamber 100 and the upper chamber 200. The gasket 400 may be made of a heat-resistant, elastic material. Examples of materials suitable for the gasket 400 include, but are not limited to, rubbers, plastics, and synthetic resins. Preferably, the gasket 400 is a plate-like member through which the base chamber 100 is held in tight contact with the upper chamber 200. The gasket 400 is held on the reagent accommodating part 300. That is, the reagent accommodating part 300 is received in the receiving chamber 110 of the base chamber 100, the gasket 400 is held on the reagent accommodating part 300, and the upper chamber 200 is arranged on the gasket 400. A space corresponding to the accommodation space 310 of the reagent accommodating part 300 may be formed in the gasket 400. The space is provided as a hole 410, as illustrated in FIG. 4. However, there is no limitation on the form of the space.

The elastic gasket 400 is arranged between the base chamber 100 and the upper chamber 200. With this arrangement, when the upper chamber 200 is pressurized, sealing is achieved by the gasket 400. This sealing can prevent external impurities from entering the reagent accommodating part 300 received in the receiving chamber 110 and a reagent received in the reagent accommodating part 300. Further details will be given below.

The jig 500 is connected to the base chamber 100, extends above the upper chamber 200, and has an internally threaded hole 530 formed in the upper portion thereof. The jig 500 may be fixedly connected to the base chamber 100 but is preferably provided as a member separate from the base chamber 100 such that it can be detached from the base chamber 100, as needed. However, there is no limitation on the structure of the jig 500.

For example, the jig 500 may have support portions 510 facing each other at both ends thereof. Each of the support portions 510 is bent in an angled C shape. The support portions 510 are connected to each other through an extension portion 520. The lateral sides of the base chamber 100 and the upper chamber 200 are held in and supported by the angled C-shaped support portions 510. A threaded hole 530 is formed in the extension portion 520. Holding portions 130 and 260 are formed at the lateral sides of the base chamber 100 and the upper chamber 200, respectively, so that the lateral sides of the chambers 100 and 200 can be held in the support portions 510. However, the formation of the holding portions may be omitted.

The jig 500 illustrated in FIGS. 3 and 4 may be provided in plurality. In this case, the pressurization part 600 may be provided in plurality so as to correspond to the jigs 500. However, there is no limitation on the numbers of the jigs and the pressurization parts.

The pressurization part 600 pressurizes the upper chamber 200 so that the upper chamber 200, the gasket 400, and the base chamber 100 can be brought into tight contact with each other.

The pressurization part 600 may include a threaded portion 610 screwed into the threaded hole 530 of the jig 500 and a head 620 provided on the threaded portion 610. Due to this construction, the pressurization part 600 may be displaced relative to the jig 500 by turning of the head 620. That is, when the head 620 is turned in one direction, the pressurization part 600 is displaced downward to pressurize the upper chamber 200. When the head 620 is turned in the opposite direction, the pressurization part 600 is displaced upward to release the pressurization.

Preferably, the upper chamber 200 includes a body part 210, a pressurization flap 220 pressurized upon contact with the pressurization part 600, and a receiving recess 230 formed in the body part 210 to receive the pressurization flap 220, as illustrated in FIG. 4.

The body part 210 constitutes the body of the upper chamber 200. The receiving recess 230 is formed in a portion of the body part 210 to receive the pressurization flap 220 in contact with the pressurization part 600. That is, when the pressurization part 600 is moved downward along with the turning of the head 620 to pressurize the upper chamber 200, it pressurizes the pressurization flap 220 provided in the receiving recess 230 of the upper chamber 200 instead of coming into direct contact with the body part 210 of the upper chamber 200, and as a result, the upper chamber 200 is pressurized as a whole. This design prevents the pressurization part 600 from coming into direct contact with the overall structure of the upper chamber 200 and pressurizing the upper chamber 200. Thus, despite repeated operations, the overall structure of the upper chamber 200 can be protected from damage. That is, only the pressurization flap 220 in direct contact with the pressurization part 600 may be damaged by repeated operations. In this case, the pressurization flap 220 is replaced with a new one without the need to replace the overall structure of the upper chamber 200, achieving improved economic efficiency in terms of management, maintenance, and repair.

Preferably, a connection hole 240 connected to the receiving recess 230 is formed at one side of the body part 210. A fixing member 250 is inserted into the connection hole 240. A fixing groove 222 is formed on the side surface of the pressurization flap 220 and is connected to the fixing member 250. When the pressurization flap 220 is arranged in the receiving recess 230 and the fixing member 250 is then inserted into the fixing groove 222 through the connection hole 240, the pressurization flap 220 can be fixed. With this configuration, despite contact between the pressurization part 600 and the pressurization flap 220 and a screwing action of the pressurization part 600, the pressurization flap 220 can be prevented from unnecessary displacement or dislocation.

According to one preferred embodiment, first irregularities are formed at the upper and lower sides of the gasket 400 in contact with the upper chamber 200 and the base chamber 100, respectively, and second irregularities corresponding to the first irregularities are formed at the upper side of the base chamber 100 and the lower side of the upper chamber 200, which are in contact with the gasket 400. That is, the formation of the first irregularities and the second irregularities ensures more reliable close contact between the gasket 400 and the base chamber 100 and between the gasket 400 and the upper chamber 200. Although there are tolerances between the gasket 400 and the base chamber 100 and between the gasket 400 and the upper chamber 200, the irregularities increase the penetration paths of impurities to more effectively block the penetration of impurities and prevent impurities from reaching a reagent.

While the present invention has been described herein with reference to its preferred embodiments, these embodiments do not serve to limit the invention. It should be understood that various modifications can be made by those skilled in the art without departing from the subject matter of the invention as defined in the appended claims. Such modifications should not be separately understood from the spirit and prospect of the invention.

The present invention will be explained in more detail with reference to the following examples, including test examples. However, these examples are not intended to limit the invention.

Manufacturing Example 1: Manufacture of Sealing Chamber

In this example, a sealing chamber 1 in which a plate for next-generation sequencing can be mounted was manufactured. The sealing chamber was made of a highly thermally conductive metal. The sealing chamber was designed to use a rubber cover capable of preventing a PCR solution from leaking between the sealing chamber and the plate for next-generation sequencing. A portion of the lateral side of the cover was exposed to the lateral side of a gasket.

The construction of the sealing chamber is illustrated in FIGS. 3 and 4. Specifically, the sealing chamber includes a base chamber 100, an upper chamber 200, a reagent accommodating part 300, a gasket 400, a jig 500, and a pressurization part 600.

Example 1: Sequencing of Nucleic Acid Molecules Through 454 Sequencing

Adaptor sequences proposed in next-generation sequencing assays were attached to acquired DNA libraries before sequencing. PCR assembly or ligation was used to attach the adaptor sequences. 20 bp long barcode sequences were added and their length was controllable.

The adaptor sequences were attached by PCR assembly. The PCR solution had the following composition: 10 µl of 2× Pfu polymerase master mix, 1 µl of 10 µM adaptor forward primer, 1 µl of 10 µM adaptor reverse primer, and 5 µl of distilled water. The Pfu polymerase master mix was 2× Pfu polymerase premix available from Solgent. Each primer included 454 adaptor sequences, barcode sequences, and sequences complementary to the terminal sequences of the DNA library. The actual sequences of the primers were CCATCTCATCCCTGCGTGTCTCCGACTCA-GNNNNNNNNNNNNNNNNNNNNA CGTACGACA-GAGTACTCGT (SEQ ID No. 1) for the adaptor forward primer and CCTATCCCCTGTGTGCCTTGGCAGTCTCA-GNNNNNNNNNNNNNNNNNNNNT CGAACTAATCG-GATTGCG (SEQ ID No. 2) for the adaptor reverse primer. At this time, the PCR was performed under the following conditions: 95° C. for 10 min for initial DNA denaturation, 15-20 cycles of 95° C. for 30 s, 58° C. for 30 s, and 72° C. for 45 s, and 72° C. for 10 min for final extension. The adaptor-attached DNA libraries were sequence-verified by Sanger sequencing to determine whether the adaptor sequences were attached. The 454 adaptor-attached DNA libraries were subjected to 454 sequencing.

TABLE 1

| | |
|---|---|
| F1_1 (SEQ ID No. 3) | CTCTTCTCCGCCGCAAAATCTGGCAACTGAAAGAGCTGGGTTATGCAGCCGTGG ATGATGAAACCACGCAACAGACAATGCGTGAGTTAAAAGAACTGGGCTACACT TCGGAGCCGCACGCTGCCGTAGCTTATCGTGCGCTGCGTGATCAGTTGAATCCA GGCGAATATGGCTTGTTCCTCGGCACCGCGCATCCGGCGAAATTTAAAGAGAGC GTGGAAGCGATTCTCGGTGAAACGTTGGATCTGCCAAAAGAGCTGGCAGAACG TGCTGATTTACCCTTGCTTTCACATAATCTGCCCGCCGATTTTGAGAGACC |
| F1_2 (SEQ ID No. 4) | CTCTTCTCTTGAAGGCACCGATACGCTGGCGTATACCGATGCGCAGTATCAACA GCTTGCGGCGGTTACGCGCGCACTGATTGATTGCTATCCGGATATCGCTAAAAA CATGACGGGCCATTGTGATATTGCGCCGGATCGCAAAACCGATCCCGGTCCTGC ATTTGATTGGGCACGCTTTCGTGTGCTGGTCAGCAAGGAGACAACATGACGCTA TTTACAACCTTACTGGTGTTAATTTTCGAGCGCCTGTTTAAGTTGGGCGAGCACT GGCAGCTTGATCATCGTCTTGAAGCGTTCTTTCGCCGCGTGAGAGACC |

TABLE 1-continued

| | |
|---|---|
| F1_3 (SEQ ID No. 5) | CTCTTCTGCCGCCGACTCAAACACCTCGTCCGTCACCTCCATCCCGCCGTGCAG ATCGAACTCCTTCGCCATCTGCTTGCCGAGCGTAGTCTGGTCGTCATGGAACGC CGGCAGACAGTGCAGGAACTTCACGTTCGGGTTGTCGGTCAGCGCCATCATCTG CGCGTTCACCTGATACCCGCGCAGCAGCGCAATGCGCTCTGCCCACTTCTCTTT GGCCTCGCCCATCGACACCCACACGTCGGTATAGATAAAGTCCGCGCCCTTAAC GCCTGCCGCCACGTCTTCCGTCAGAGTAATTTTCCCGCCGTGAGAGACC |
| F2_1 (SEQ ID No. 6) | CTCTTCTGCGGGTAACCACGCCCTGGCGAATGTGTTCTACCAGCGGCGCATGGC AATCACTCAGCGAGCTCGACGCCAGGGTCAGGTTTTTAAAGCCCATCTTCGCGA TGACGTCCATCACCATATTGACGGTCAGGTCACCGCCACGGAAAGCGTGATGG AACGAAACCGTCATGCCGTCCTGTAAACCTGAGCGACGAATCGCTTCTTCCAGG TTGGCGCACAGTTTGCGATCGCGCGCTTTTTCAGCCTGGTAGGTTTGCTTTGGCG AGTTCTGGAAAGCGGCAAGATCGCATTCAGCGCGACGATTCCAGAGACC |
| F2_2 (SEQ ID No. 7) | CTCTTCTAGCTGGATAACTTCCGTCAGGAAGTTCACGGCAATGGCCTCTCATCG TATCCGCACCCGAAACTGATGCCGGAATTCTGGCAGTTCCCGACCGTATCAATG GGTCTGGGTCCGATTGGTGCTATTTACCAGGCTAAATTCCTGAAATATCTGGAA CACCGTGGCCTGAAAGATACCTCAAAACAAACCGTTTACGCGTTCCTCGGTGAC GGTGAAATGGACGAACCGGAATCGAAAGGTGCGATCACCATCGCTACCCGTGA AAAACTGGATAACCTGGTCTTCGTTATCAACTGTAACCTGCAGAGAGACC |
| F3_1 (SEQ ID No. 8) | CTCTTCTCCCGGCGTTGATGGCGTGAACAAAACAATGCTACAGGCCCGTCTGGC TGTTGAGCTGCAAATCCTCCGTGATGAATTACTCTCAGGCCACTACCAGCCCTT GCCCGCCCGTCGCGTTTACATCCCTAAAAGCAACGGCAAACTGCGCCCACTGGG TATCCCCGCGTTGCGCGATCGTATTGTTCAGCGCGCCATGCTGATGGCGATGGA GCCGATTTGGGAGAGTGATTTTCATACGCTCTCATATGGCTTCCGCCCTGAGCG CAGTGTCCACCACGCGATCCGCACGGTGAAATTACAGCTCACAGAGACC |
| F3_2 (SEQ ID No. 9) | CTCTTCTAACGCCTGCCGCCACGTCTTCCGTCAGAGTAATTTTCCCGCCGTGCTT CTCCGCCAGCGCGCTGCACTCCGCCACCAGGCTCTCTTCCGGCCAGCAGGCTTT CGGGGCCAACAGGCGCAGATCCAGCCCGGTCAGCGCCGCCGCTTCCAGCATCG AGTTGCCCATGTTGTTGCGCGCATCGCCCGCGTAGACCAGCGTCATCTCGTTAA ACGCCTTGCCCGGCAGGTGCTCCTGCATGGTCATCAGGTCCGCCAGCAGCTGGG TCGGGTGGAACTCGTTGGTCAGCCCGTTCCACACCGGCACGCAGAGACC |
| F4_1 (SEQ ID No. 10) | CTCTTCTCAGTGCGAGTTCCGGCTGACCAGGAATGTAACGTTGCGCATGCAGCC ACCAGTAGAGGGCATTGCTTCCCAGTCCACGTTTTTCTGCCTGTTGTAGCCAGC GATCGCGAGCCGCACCATTTCCTGCCGCCTGGGCGGTATTGGCAGCAGCAAGCA GATCCTCATTGCTCATGTCGTGAAGACTGATTTTCTGCCAGGCCGCCAGTGCGG TGGCGTAGTCCTCAACCTGATACGCCTGATAGGCTACCGCACGATGTTGCCAGG CGCTCGGTTGGCGTTGTTCGGCCTGAAGCCATGCATACAACGAGAGACC |

Example 2: Amplification of the Sequence-Verified Nucleic Acid Molecules in 454 Picotilter Plate The sequencing plate having undergone 454 sequencing was mounted in the sealing chamber manufactured in Manufacturing Example 1, followed by sealing. Thereafter, a PCR solution was injected into the sealing chamber through the lateral side of the rubber cover exposed to the lateral side of the sealing chamber using a syringe. The PCR solution was composed of a DNA polymerase, dNTPs, a primer including adaptor sequences proposed in next-generation sequencing, and a buffer or its corresponding PCR solution master mix.

The PCR solution had the following composition: 600 µl of 2× Pfu polymerase master mix, 15 µl of 100 µM primer, and 585 µl of distilled water. After the sealing chamber containing the PCR solution was immersed in a water bath, the nucleic acid fragments were amplified and extended. The Pfu polymerase master mix was 2× Pfu polymerase premix available from Solgent. The primer sequence was the 454 For sequence of 454 adaptor sequences (CCATCTCATC-CCTGCGTGTCTCCGACTCAG (SEQ ID No. 11)). The PCR was performed under the following conditions: 95° C. for 10 min for initial DNA denaturation, 3-10 cycles of 95° C. for 5 min, 60° C. for 5 min, and 72° C. for 5 min, and 72° C. for 10 min for final extension.

Example 3: Identification of the Nucleic Acid Molecules Amplified in the 454 Picotilter Plate After completion of the reaction, the sealing chamber was withdrawn from the water bath, and the amplified and extended nucleic acid fragments, together with the PCR solution, were retrieved through the lateral side of the rubber cover exposed to the lateral side of the sealing chamber using a syringe (see FIG. 8). The retrieved DNA libraries had different features from the DNA libraries before sequencing. That is, the total number of the kinds of the DNA libraries was reduced to the number of reads for next-generation sequencing and the sequences of the DNA libraries were all known.

After retrieval, the reduced DNA libraries were selectively amplified by the primers attached with the barcode sequences. The results are shown in FIG. 9. The randomly selected barcode sequences were verified by next-generation sequencing. The results indicate that the randomly selected barcode sequences were verified by next generation sequencing, the retrieved nucleic acids were selectively amplified with the verified random sequences, showing that the data obtained by sequencing were identical to the sequences of the retrieved nucleic acids. The sequences of the amplified individual nucleic acid fragments were verified by Sanger sequencing. These results reveal that the retrieval yields of individual nucleic acid fragments from the reduced DNA libraries were markedly improved compared to the retrieval yields from an entire pool of DNA libraries according to the conventional method. According to the conventional method, the retrieval yields of individual nucleic acid fragments from an entire pool of DNA libraries were about 77% ('Shotgun DNA synthesis' for the high-throughput construction of large DNA molecules, 2012 Nucleic Acids Research, Kim et al.). In contrast, the use of the method according to the present invention enabled the retrieval of all nucleic acid fragments (see FIG. 10).

Example 4: Direct Retrieval of Sequence-Verified Nucleic Acid Fragments from Illumina Flow Cell About 300 bp long nucleic acid fragments were placed in a sequencing plate (PE MiSeq Flow Cell, Illumina) and sequenced using Illumina PE MiSeq. Then, a pipette was used to inject a PCR solution into the inlet of the sequencing plate containing the sequenced nucleic acid fragments. The PCR solution had the following composition: 1 μl of 10 μM Illumina forward primer (SEQ ID No. 12: AATGATACG-GCGACCACCGA), 1 μl of 10 μM Illumina reverse primer (SEQ ID No. 13: CAAGCAGAAGACGGCATACG), 10 μl of 2× KAPA HiFi HotStart ReadyMix, and 8 μl of distilled water.

Then, the inlet of the sequencing plate was closed with a tape (Microseal B Adhesive Sealer, BIO-RAD), the sequencing plate was placed in a water bath, followed by amplification of the nucleic acid fragments. At this time, the reaction was performed under the following conditions: 95° C. for 10 min for initial DNA denaturation and 3-10 cycles of 95° C. for 5 min and 70° C. for 5 min.

After completion of the reaction, the sequencing plate was taken out of the water bath, the sealing tape was removed from the inlet, the amplified and extended nucleic acid fragments, together with the PCR solution, were retrieved using a pipette, followed by purification. A chromatogram of the retrieved nucleic acid fragments measured using Agilent TapeStation and information on the concentrations obtained from the peaks of the chromatogram are shown in FIG. 11. Referring to FIG. 11, the peak corresponding to the retrieved DNA library is marked by 322 in the chromatogram. The number 322 represents the length of the measured DNA library. The bottom table of FIG. 11 shows information on the concentration and molarity of the 322 bp long DNA library. The results demonstrate retrieval of the sequence-verified nucleic acid fragments.

Example 5: Amplification of the Sequence-Verified Nucleic Acid Molecules in Illumina Flow Cell The individual nucleic acid fragments were retrieved from the DNA libraries collected and purified in Example 4 by two amplification processes. First, all nucleic acid fragments in the collected and purified DNA libraries were amplified by the following procedure. A PCR solution tube containing 5 μl of DNA libraries, 3 μl of distilled water, 1 μl of 10 μM Illumina forward primer (SEQ ID No. 12: AATGATACG-GCGACCACCGA), 1 μl of 10 μM Illumina reverse primer (SEQ ID No. 13: CAAGCAGAAGACGGCATACG), and 10 μl of 2× KAPA HiFi HotStart ReadyMix was maintained at 95° C. for 10 min. Thereafter, 10 cycles of 95° C. for 5 min, 60° C. for 5 min, and 72° C. for 5 min were repeated. Final extension was performed at 72° C. for 10 min. By this process, the total amount of the DNA libraries was amplified, which facilitated the subsequent amplification of the individual nucleic acid fragments.

Next, 48 individual nucleic acid fragments were randomly selected from the amplified DNA libraries and were amplified by the following procedure. 1 μl of each amplified DNA library, 1 μl of 10 μM each forward primer (Fwd_1-48 sequences in Table 2), 1 μl of 10 μM each reverse primer (Rev_1-48 sequences in Table 2), 7 μl of distilled water, and 10 μl of 2× KAPA HiFi HotStart ReadyMix were mixed together to prepare a PCR solution. The PCR solution was maintained at 95° C. for 10 min. Thereafter, 30 cycles of 95° C. for 5 min, 60° C. for 5 min, and 72° C. for 5 min were repeated. (In the case that nucleic acid fragments were not obtained, 5 more cycles were repeated.) Final extension was performed at 72° C. for 10 min. For efficiency comparison, 48 individual nucleic acid fragments were amplified from the original DNA libraries, which were not collected from the sequencing plate, in the same manner as described above. The amplified individual nucleic acid fragments were identified and purified through gel electrophoresis. The results are shown in FIG. 12. The sequences of the individual nucleic acid fragments were verified by Sanger sequencing.

As a result, 42 out of the 48 individual nucleic acid fragments were retrieved error-free from the DNA libraries before retrieval of the nucleic acid fragments, i.e. unreduced DNA libraries. The retrieval rate was 85.4% (see (a) of FIG. 12). 47 out of the 48 individual nucleic acid fragments were retrieved error-free from the DNA libraries after retrieval of the nucleic acid fragments according to the present invention. The retrieval rate was 97.9% (see (b) of FIG. 12). These results reveal that the methods of the present invention enable highly efficient retrieval of individual nucleic acid fragments.

TABLE 2

| | | | | |
|---|---|---|---|---|
| Fwd_1 (SEQ ID No. 14) | GAGCACGCCTTTATATGTA | Rev_1 (SEQ ID No. 62) | | TGAAATTGTTTGGGACCTG |
| Fwd_2 (SEQ ID No. 15) | CAGTACTTTTGGGTAGGCC | Rev_2 (SEQ ID No. 63) | | TTACAATATTCGGCACTCG |
| Fwd_3 (SEQ ID No. 16) | CGATATGGATAGTTATTAT | Rev_3 (SEQ ID No. 64) | | TTTGACCCTTGCTAAATGC |
| Fwd_4 (SEQ ID No. 17) | GGGAAAAATTCGGTATTTT | Rev_4 (SEQ ID No. 65) | | TGTGATTGTTCGTGAAAGT |
| Fwd_5 (SEQ ID No. 18) | GTGGAGATTTCCCTACTGG | Rev_5 (SEQ ID No. 66) | | AAATACCCGTTCTAACGGA |
| Fwd_6 (SEQ ID No. 19) | TCTTAAGTCTTTTTAAGCA | Rev_6 (SEQ ID No. 67) | | AGCAATCTTTGTAGAAGTC |
| Fwd_7 (SEQ ID No. 20) | TGCTAGATGTTGAAATTAA | Rev_7 (SEQ ID No. 68) | | GATGATCTCTCGGGAAAAT |

TABLE 2-continued

| | | | |
|---|---|---|---|
| Fwd_8 (SEQ ID No. 21) | TACAACTTCTTCTCATTCG | Rev_8 (SEQ ID No. 69) | ATTTATGGGTTTTAAGTGC |
| Fwd_9 (SEQ ID No. 22) | TCCGATAAGTCCGTACATA | Rev_9 (SEQ ID No. 70) | AGTAATCATTTCTTAGGTC |
| Fwd_10 (SEQ ID No. 23) | GCCCAAGGATTTCGACAAC | Rev_10 (SEQ ID No. 71) | CTTGAAGGCTTAAGATTAT |
| Fwd_11 (SEQ ID No. 24) | TTGTATGGTTTTGGATGTG | Rev_11 (SEQ ID No. 72) | GTTGAATGCTTCGTATGTT |
| Fwd_12 (SEQ ID No. 25) | TGTTAGCTGTTTTCAGTGC | Rev_12 (SEQ ID No. 73) | GCACATCTTTCGGTATCTC |
| Fwd_13 (SEQ ID No. 26) | CAATAGTTTTCGGCATTTT | Rev_13 (SEQ ID No. 74) | TGTAATGTCTGATGAACTC |
| Fwd_14 (SEQ ID No. 27) | GCCTAACAGTGCTGAAGAA | Rev_14 (SEQ ID No. 75) | ATCAAGGGCTACGGATTGC |
| Fwd_15 (SEQ ID No. 28) | CAAAACAAGTCTCCACTTG | Rev_15 (SEQ ID No. 76) | TTGGATATGTATCGACGAC |
| Fwd_16 (SEQ ID No. 29) | TTGGAGCATTGTCGAGTAG | Rev_16 (SEQ ID No. 77) | AGTAAGTCGTCCTAAGGGG |
| Fwd_17 (SEQ ID No. 30) | GATAATCACTCTCTAGAGT | Rev_17 (SEQ ID No. 78) | ATAATTTGTCTTTATCCTA |
| Fwd_18 (SEQ ID No. 31) | ATGCATGCGTTCGTACAAA | Rev_18 (SEQ ID No. 79) | TGAGATTAATGGCGACGTG |
| Fwd_19 (SEQ ID No. 32) | CAAGACTTATTTCTAGTGT | Rev_19 (SEQ ID No. 80) | TTTCATTCCTTTATAATAG |
| Fwd_20 (SEQ ID No. 33) | CCCCAGTGCTCGTCATGGT | Rev_20 (SEQ ID No. 81) | TTTAATGTTTAACTATTTA |
| Fwd_21 (SEQ ID No. 34) | CGTAAGAGCTCGTAAGACG | Rev_21 (SEQ ID No. 82) | TGTAATCCCTATACAATGA |
| Fwd_22 (SEQ ID No. 35) | CTGTATTTTTGCCAACTTT | Rev_22 (SEQ ID No. 83) | GGTAATAGGTATCGATTGG |
| Fwd_23 (SEQ ID No. 36) | GCGATAACATGGTGACCTC | Rev_23 (SEQ ID No. 84) | AATCATAACTTTGTAACTT |
| Fwd_24 (SEQ ID No. 37) | CACGAATCTTAACAATGTG | Rev_24 (SEQ ID No. 85) | AATAAATATTGTCGATTCA |
| Fwd_25 (SEQ ID No. 38) | GTTGATCCCTGCCCACGGT | Rev_25 (SEQ ID No. 86) | TCTAATCTTTAAGATGTGA |
| Fwd_26 (SEQ ID No. 39) | AATTACTGGTGGACAACGG | Rev_26 (SEQ ID No. 87) | GATTATTATTTTCAAATTG |
| Fwd_27 (SEQ ID No. 40) | AAATACGCGTTGAGAAGTA | Rev_27 (SEQ ID No. 88) | ATACAGGGTTAGCGAGCTG |
| Fwd_28 (SEQ ID No. 41) | CCCTAACTGTTTTAACTGG | Rev_28 (SEQ ID No. 89) | AGTTATTATTTGTTAGCGC |
| Fwd_29 (SEQ ID No. 42) | TTATATCTATCTTTACGTG | Rev_29 (SEQ ID No. 90) | GGATATGTTTAGAAAAAAG |
| Fwd_30 (SEQ ID No. 43) | TCTCACCAATGTGGAGAGG | Rev_30 (SEQ ID No. 91) | GGTCATATATAGAAAATAG |
| Fwd_31 (SEQ ID No. 44) | TGAAACCATTAAGCAATTT | Rev_31 (SEQ ID No. 92) | TTTTATTTTTTACAACGCA |
| Fwd_32 (SEQ ID No. 45) | TTTTATTTATTCTTAGGGT | Rev_32 (SEQ ID No. 93) | TAGGAGTTGTTAGGACCGT |
| Fwd_33 (SEQ ID No. 46) | TATCAGGGGTTTCTAGTTT | Rev_33 (SEQ ID No. 94) | TATCAGAAGTTGCAATTCT |

TABLE 2-continued

| | | | |
|---|---|---|---|
| Fwd_34 (SEQ ID No. 47) | CCTGAGTTATGGAGAGCAC | Rev_34 (SEQ ID No. 95) | CTGAACCTCTAATCATCGG |
| Fwd_35 (SEQ ID No. 48) | GACAACAACTATGGATTAC | Rev_35 (SEQ ID No. 96) | AGGCACTGGTCGTCAAGAT |
| Fwd_36 (SEQ ID No. 49) | CCGTATCCATGAAGACGTT | Rev_36 (SEQ ID No. 97) | GGCAATAGGTGGGAAGGGT |
| Fwd_37 (SEQ ID No. 50) | CAAAATGGCTAAAGACTAA | Rev_37 (SEQ ID No. 98) | TAACAAATATCGATATCTA |
| Fwd_38 (SEQ ID No. 51) | AGAAATGCATGAGTAAAGG | Rev_38 (SEQ ID No. 99) | TTTTAACGCTAGTTACCCA |
| Fwd_39 (SEQ ID No. 52) | GTGTATTGTTGTAAATAAG | Rev_39 (SEQ ID No. 100) | CTTGATAATTTGAGATACT |
| Fwd_40 (SEQ ID No. 53) | AAGGAGATCTACCCACTAG | Rev_40 (SEQ ID No. 101) | AATTAATGGTATTGATTAT |
| Fwd_41 (SEQ ID No. 54) | TCCCAATCTTCCCTACAAG | Rev_41 (SEQ ID No. 102) | AAAGATGTTTGACAAACGC |
| Fwd_42 (SEQ ID No. 55) | TGTTAAAAATATTTATTTT | Rev_42 (SEQ ID No. 103) | TCACAGGGTTGTTGATCTT |
| Fwd_43 (SEQ ID No. 56) | AGTCATTCTTGGTTATATT | Rev_43 (SEQ ID No. 104) | TTCGACATCTTGACATGAC |
| Fwd_44 (SEQ ID No. 57) | ATAAAGTTTTGTATAATTC | Rev_44 (SEQ ID No. 105) | ATATATTGTTTTCAGCGTA |
| Fwd_45 (SEQ ID No. 58) | CACTAGAATTCCGAAGGGT | Rev_45 (SEQ ID No. 106) | TGATAATCATGTTGACACT |
| Fwd_46 (SEQ ID No. 59) | TTTGATGTTTGTTTACACT | Rev_46 (SEQ ID No. 107) | GAAGAAGTTTTCCAAGGCC |
| Fwd_47 (SEQ ID No. 60) | TTTAAAGGATCTGTATGTG | Rev_47 (SEQ ID No. 108) | GCTTATGAATCGCAATACA |
| Fwd_48 (SEQ ID No. 61) | AAAAACATGTAGTCAAACG | Rev_48 (SEQ ID No. 109) | TTTTACCCGTGGGAAACCC |

Example 6: Preparation for Ion Torrent Sequencing and Acquisition of Reduced Libraries DNA libraries were synthesized using a microchip array and DNA fragments were acquired by cleaving the DNA libraries from the chips. Referring to FIG. 13, each DNA library included 19 base pair (bp) long barcode sequences and 20 bp sequences complementary to proton adaptor sequences at both ends. The length of the barcode sequences was controllable upon initial design. Adaptor sequences proposed in next-generation sequencing assays were attached before sequencing. PCR assembly or ligation was used to attach the adaptor sequences. When barcode sequences and sequences complementary to adaptor sequences are absent in the acquired DNA libraries, they can also be added in this step.

The adaptor sequences were attached by PCR assembly. The PCR solution had the following composition: 0.5 µl of template, 10 µl of 2× KAPA Hifi polymerase mix, 1 µl of 10 µM adaptor forward primer, 1 µl of 10 µM adaptor reverse primer, and 7.5 µl of distilled water. The KAPA Hifi polymerase mix was a 2× KAPA Hifi HotStart PCR kit with dNTPs available from KAPA Biosystems. Each primer included sequences complementary to the terminal sequences of the DNA library as proton adaptor sequences. The actual sequences of the primers were CCATCTCATC-CCTGCGTGTCTCCGACTCAGTGAGCGGAACGAT (SEQ ID No. 110) for the adaptor forward primer and CCACTACGCCTCCGCTTTCCTCTCTATGGGCA-GTCGGTGAT (SEQ ID No. 111) for the adaptor reverse primer. At this time, the PCR was performed under the following conditions: 95° C. for 3 min for initial DNA denaturation, 15-20 cycles of 95° C. for 30 s, 60° C. for 30 s, and 72° C. for 30 s, and 72° C. for 10 min for final extension.

The DNA libraries having undergone PCR had proton adaptor sequences in common, which are complementary to single-stranded DNA connected to sequencing beads.

The DNA libraries having undergone PCR were mixed with ion sphere particles (ISP) as sequencing beads and PCR-related reagents (including mineral oil) for Ion-Torrent Proton sequencing. The DNA libraries attached with the sequencing beads (1:1) were amplified using an Ion One-Touch™ 2 system. At this time, only one kind of DNA library is theoretically present in one sequencing bead.

Thereafter, intact DNA was obtained with a correct combination of both adaptor sequences of the DNA library. The opposite portions of the DNA libraries attached with the sequencing beads had sequences complementary to Streptavidin C1 beads tending to stick to a magnet and were thus attached with Streptavidin C1 beads. Thereafter, the attached Streptavidin C1 beads were stuck to a magnet and washed.

Only intact DNA was left and the remainder was discarded. This process was automatically performed using an Ion OneTouch™ ES system.

Thereafter, the double-stranded DNA libraries attached with the sequencing beads were separated into single-stranded DNA by denaturation with NaOH. The single-stranded DNA attached with the adaptor sequences was sequence-verified by Ion torrent proton sequencing, and at the same time, a solution of the single-stranded DNA separated from the sequencing beads was collected. Since the solution contained the enzyme and buffer solution used in the amplification and separation processes as well as the single-stranded nucleic acid fragments, DNA purification was performed to retrieve the pure single-stranded nucleic acid fragments.

Example 7: Amplification of Desired Nucleic Acid Fragments from the Reduced DNA Libraries Obtained During Ion Torrent Sequencing The single-stranded nucleic acid fragments obtained in Example 6 were used as templates for PCR reaction with a PCR instrument.

The PCR solution had the following composition: 1 µl of template, 10 µl of 2× KAPA Hifi polymerase mix, 1 µl of 10 µM forward primer, 1 µl of 10 µM reverse primer, and 7 µl of distilled water. The KAPA Hifi polymerase mix was a 2× KAPA Hifi HotStart PCR kit with dNTPs available from KAPA Biosystems. The primers had 20 bp long sequences complementary to the adaptor sequences included in the original DNA libraries. The actual sequences of the primers were GACTCAGTGAGCGGAACGAT (SEQ ID No. 112) for the forward primer and CTCTATGGGCAGTCGGTGAT (SEQ ID No. 113) for the reverse primer. At this time, the PCR was performed under the following conditions: 95° C. for 3 min for initial DNA denaturation, 15-20 cycles of 95° C. for 30 s, 60° C. for 30 s, and 72° C. for 30 s, and 72° C. for 10 min for final extension.

Example 8: Sequence Verification of the Amplified Nucleic Acid Fragments Obtained During Ion Torrent Sequencing The PCR amplification products obtained in Example 7 were identified by electrophoresis of the PCR solution after the reaction on an agarose gel. As a result of the electrophoresis, bands could be confirmed at expected sizes of the nucleic acid fragments included in the libraries (see FIG. 14). The bands were selectively purified to retrieve the amplified library nucleic acid fragments only. This indicates that the number of all DNA libraries was reduced to the number of the sequencing beads synthesized for next-generation sequencing.

After retrieval, the reduced DNA libraries were separated into individual DNA fragments through TOPO cloning and PCR (see FIG. 15). The sequences of the separated individual DNA fragments were verified by Sanger sequencing and were compared with the contents of the original DNA libraries (see FIG. 16), showing successful retrieval of the desired nucleic acid fragments.

INDUSTRIAL APPLICABILITY

According to the present invention, all DNA libraries are reduced by sequencing, achieving increased retrieval yields of final target nucleic acid fragments. In addition, the methods of the present invention enable a more effective use of nucleic acid fragments, which have previously been wasted after sequencing. Furthermore, the sealing chambers of the present invention can be used as amplifiers capable of amplifying nucleic acid fragments whose sequences are verified by parallel synthesis. The use of the amplifiers allows rapid amplification of sequence-verified nucleic acid fragments, enabling the processing of a large amount of nucleic acid fragments in a more effective manner. Therefore, the methods and apparatuses of the present invention are expected to be industrially very useful.

| [Explanation of reference numerals] | |
| --- | --- |
| 1: Sealing chamber | 100: Base chamber |
| 110: Receiving chamber | 120: Guide portions |
| 130: Holding portion | 200: Upper chamber |
| 210: Body part | 220: Pressurization flap |
| 222: Fixing groove | 230: Receiving recess |
| 240: Connection hole | 250: Fixing member |
| 260: Holding portion | 300: Reagent accommodating part |
| 310: Accommodation space | 400: Gasket |
| 410: Hole | 500: Jig |
| 510: Support portions | 520: Extension portion |
| 530: Threaded hole | 600: Pressurization part |
| 610: Threaded portion | 620: Head |

The invention claimed is:

1. A method for retrieving nucleic acid fragments, comprising (a) preparing sequencing beads, wherein the sequencing beads are beads that are attached with amplified double-stranded DNA libraries, wherein the amplified double-stranded DNA libraries include sequenced DNAs after sequencing, (b) collecting single-stranded nucleic acid fragments separated from the sequencing beads to provide reduced DNA libraries, (c) amplifying the collected single-stranded nucleic acid fragments, and (d) retrieving the amplified nucleic acid fragments.

2. The method according to claim 1, further comprising (e) acquiring desired nucleic acid fragments among the retrieved nucleic acid fragments.

3. The method according to claim 2, wherein when the amplified nucleic acid fragments are tagged with specific barcode sequences, the desired nucleic acid fragments are acquired using sequences having a homology to the barcode sequences.

* * * * *

SEQUENCE LISTING

<160> NUMBER OF SEQ ID NOS: 121

<210> SEQ ID NO 1
<211> LENGTH: 70
<212> TYPE: DNA
<213> ORGANISM: Artificial Sequence
<220> FEATURE:
<223> OTHER INFORMATION: adaptor forward primer
<220> FEATURE:
<221> NAME/KEY: misc_feature
<222> LOCATION: (31)..(50)
<223> OTHER INFORMATION: n is a, c, g, or t

<400> SEQUENCE: 1
ccatctcatc cctgcgtgtc tccgactcag nnnnnnnnnn nnnnnnnnnn acgtacgaca        60
gagtactcgt        70

```
<210> SEQ ID NO 2
<211> LENGTH: 69
<212> TYPE: DNA
<213> ORGANISM: Artificial Sequence
<220> FEATURE:
<223> OTHER INFORMATION: adaptor reverse primer
<220> FEATURE:
<221> NAME/KEY: misc_feature
<222> LOCATION: (31)..(50)
<223> OTHER INFORMATION: n is a, c, g, or t

<400> SEQUENCE: 2
cctatcccct gtgtgccttg gcagtctcag nnnnnnnnnn nnnnnnnnnn tcgaactaat    60
cggattgcg                                                            69

<210> SEQ ID NO 3
<211> LENGTH: 319
<212> TYPE: DNA
<213> ORGANISM: Artificial Sequence
<220> FEATURE:
<223> OTHER INFORMATION: synthetic primer

<400> SEQUENCE: 3
ctcttctccg ccgcaaaatc tggcaactga aagagctggg ttatgcagcc gtggatgatg    60
aaaccacgca acagacaatg cgtgagttaa agaactggg ctacacttcg gagccgcacg   120
ctgccgtagc ttatcgtgcg ctgcgtgatc agttgaatcc aggcgaatat ggcttgttcc   180
tcggcaccgc gcatccggcg aaatttaaag agagcgtgga agcgattctc ggtgaaacgt   240
tggatctgcc aaaagagctg gcagaacgtg ctgatttacc cttgctttca cataatctgc   300
ccgccgattt tgagagacc                                                319

<210> SEQ ID NO 4
<211> LENGTH: 319
<212> TYPE: DNA
<213> ORGANISM: Artificial Sequence
<220> FEATURE:
<223> OTHER INFORMATION: synthetic primer

<400> SEQUENCE: 4
ctcttctctt gaaggcaccg atacgctggc gtataccgat gcgcagtatc aacagcttgc    60
ggcggttacg cgcgcactga ttgattgcta tccggatatc gctaaaaaca tgacgggcca   120
ttgtgatatt gcgccggatc gcaaaaccga tcccggtcct gcatttgatt gggcacgctt   180
tcgtgtgctg gtcagcaagg agacaacatg acgctattta caaccttact ggtgttaatt   240
ttcgagcgcc tgtttaagtt gggcgagcac tggcagcttg atcatcgtct tgaagcgttc   300
tttcgccgcg tgagagacc                                                319

<210> SEQ ID NO 5
<211> LENGTH: 319
<212> TYPE: DNA
<213> ORGANISM: Artificial Sequence
<220> FEATURE:
<223> OTHER INFORMATION: synthetic primer

<400> SEQUENCE: 5
ctcttctgcc gccgactcaa acacctcgtc cgtcacctcc atcccgccgt gcagatcgaa    60
ctccttcgcc atctgcttgc cgagcgtagt ctggtcgtca tggaacgccg gcagacagtg   120
caggaacttc acgttcgggt tgtcggtcag cgccatcatc tgcgcgttca cctgataccc   180
gcgcagcagc gcaatgcgct ctgcccactt ctctttggcc tcgcccatcg acacccacac   240
```
gtcggtatag ataaagtccg cgcccttaac gcctgccgcc acgtcttccg tcagagtaat   300
tttcccgccg tgagagacc                                                319

<210> SEQ ID NO 6
<211> LENGTH: 319
<212> TYPE: DNA
<213> ORGANISM: Artificial Sequence
<220> FEATURE:
<223> OTHER INFORMATION: synthetic primer

<400> SEQUENCE: 6
ctcttctgcg ggtaaccacg ccctggcgaa tgtgttctac cagcggcgca tggcaatcac    60
tcagcgagct cgacgccagg gtcaggtttt taaagcccat cttcgcgatg acgtccatca   120
ccatattgac ggtcaggtca ccgccacgga aagcgtgatg gaacgaaacc gtcatgccgt   180
cctgtaaacc tgagcgacga atcgcttctt ccaggttggc gcacagtttg cgatcgcgcg   240 cttttttcagc ctggtaggtt tgctttggcg agttctggaa agcggcaaga tcgcattcag   300
cgcgacgatt ccagagacc                                                319

<210> SEQ ID NO 7
<211> LENGTH: 319
<212> TYPE: DNA
<213> ORGANISM: Artificial Sequence
<220> FEATURE:
<223> OTHER INFORMATION: synthetic primer

<400> SEQUENCE: 7
ctcttctagc tggataactt ccgtcaggaa gttcacggca atggcctctc atcgtatccg    60
cacccgaaac tgatgccgga attctggcag ttcccgaccg tatcaatggg tctgggtccg   120
attggtgcta tttaccaggc taaattcctg aaatatctgg aacaccgtgg cctgaaagat   180
acctcaaaac aaaccgttta cgcgttcctc ggtgacggtg aaatggacga accggaatcg   240
aaaggtgcga tcaccatcgc tacccgtgaa aaactggata acctggtctt cgttatcaac   300
tgtaacctgc agagagacc                                                319

<210> SEQ ID NO 8
<211> LENGTH: 319
<212> TYPE: DNA
<213> ORGANISM: Artificial Sequence
<220> FEATURE:
<223> OTHER INFORMATION: synthetic primer

<400> SEQUENCE: 8
ctcttctccc ggcgttgatg gcgtgaacaa acaatgctca caggcccgtc tggctgttga    60
gctgcaaatc ctccgtgatg aattactctc aggccactac cagcccttgc ccgcccgtcg   120
cgtttacatc cctaaaagca acggcaaact gcgcccactg ggtatcccccg cgttgcgcga   180 tcgtattgtt cagcgcgcca tgctgatggc gatggagccg atttgggaga gtgattttca   240
tacgctctca tatggcttcc gccctgagcg cagtgtccac cacgcgatcc gcacggtgaa   300
attacagctc acagagacc                                                319

<210> SEQ ID NO 9
<211> LENGTH: 319
<212> TYPE: DNA
<213> ORGANISM: Artificial Sequence
<220> FEATURE:
<223> OTHER INFORMATION: synthetic primer

<400> SEQUENCE: 9

```
ctcttctaac gcctgccgcc acgtcttccg tcagagtaat tttcccgccg tgcttctccg      60
ccagcgcgct gcactccgcc accaggctct cttccggcca gcaggctttc ggggccaaca     120
ggcgcagatc cagcccggtc agcgccgccg cttccagcat cgagttgccc atgttgttgc     180
gcgcatcgcc cgcgtagacc agcgtcatct cgttaaacgc cttgcccggc aggtgctcct     240
gcatggtcat caggtccgcc agcagctggg tcgggtggaa ctcgttggtc agcccgttcc     300
acaccggcac gcagagacc                                                  319

<210> SEQ ID NO 10
<211> LENGTH: 319
<212> TYPE: DNA
<213> ORGANISM: Artificial Sequence
<220> FEATURE:
<223> OTHER INFORMATION: synthetic primer

<400> SEQUENCE: 10
ctcttctcag tgcgagttcc ggctgaccag gaatgtaacg ttgcgcatgc agccaccagt      60
agagggcatt gcttcccagt ccacgttttt ctgcctgttg tagccagcga tcgcgagccg     120
caccatttcc tgccgcctgg gcggtattgg cagcagcaag cagatcctca ttgctcatgt     180
cgtgaagact gattttctgc caggccgcca gtgcggtggc gtagtcctca acctgatacg     240
cctgataggc taccgcacga tgttgccagg cgctcggttg gcgttgttcg gcctgaagcc     300
atgcatacaa cgagagacc                                                  319

<210> SEQ ID NO 11
<211> LENGTH: 30
<212> TYPE: DNA
<213> ORGANISM: Artificial Sequence
<220> FEATURE:
<223> OTHER INFORMATION: synthetic primer

<400> SEQUENCE: 11
ccatctcatc cctgcgtgtc tccgactcag                                       30

<210> SEQ ID NO 12
<211> LENGTH: 20
<212> TYPE: DNA
<213> ORGANISM: Artificial Sequence
<220> FEATURE:
<223> OTHER INFORMATION: illumina foward primer

<400> SEQUENCE: 12
aatgatacgg cgaccaccga                                                  20

<210> SEQ ID NO 13
<211> LENGTH: 20
<212> TYPE: DNA
<213> ORGANISM: Artificial Sequence
<220> FEATURE:
<223> OTHER INFORMATION: illumina reverse primer

<400> SEQUENCE: 13
caagcagaag acggcatacg                                                  20

<210> SEQ ID NO 14
<211> LENGTH: 19
<212> TYPE: DNA
<213> ORGANISM: Artificial Sequence
<220> FEATURE:
<223> OTHER INFORMATION: forward primer
```

<400> SEQUENCE: 14
gagcacgcct ttatatgta                                              19

<210> SEQ ID NO 15
<211> LENGTH: 19
<212> TYPE: DNA
<213> ORGANISM: Artificial Sequence
<220> FEATURE:
<223> OTHER INFORMATION: forward primer

<400> SEQUENCE: 15
cagtactttt gggtaggcc                                              19

<210> SEQ ID NO 16
<211> LENGTH: 19
<212> TYPE: DNA
<213> ORGANISM: Artificial Sequence
<220> FEATURE:
<223> OTHER INFORMATION: forward primer

<400> SEQUENCE: 16
cgatatggat agttattat                                              19

<210> SEQ ID NO 17
<211> LENGTH: 19
<212> TYPE: DNA
<213> ORGANISM: Artificial Sequence
<220> FEATURE:
<223> OTHER INFORMATION: forward primer

<400> SEQUENCE: 17
gggaaaaatt cggtatttt                                              19

<210> SEQ ID NO 18
<211> LENGTH: 19
<212> TYPE: DNA
<213> ORGANISM: Artificial Sequence
<220> FEATURE:
<223> OTHER INFORMATION: forward primer

<400> SEQUENCE: 18
gtggagattt ccctactgg                                              19

<210> SEQ ID NO 19
<211> LENGTH: 19
<212> TYPE: DNA
<213> ORGANISM: Artificial Sequence
<220> FEATURE:
<223> OTHER INFORMATION: forward primer

<400> SEQUENCE: 19
tcttaagtct ttttaagca                                              19

<210> SEQ ID NO 20
<211> LENGTH: 19
<212> TYPE: DNA
<213> ORGANISM: Artificial Sequence
<220> FEATURE:
<223> OTHER INFORMATION: forward primer

<400> SEQUENCE: 20
tgctagatgt tgaaattaa                                              19

<210> SEQ ID NO 21
<211> LENGTH: 19

```
<212> TYPE: DNA
<213> ORGANISM: Artificial Sequence
<220> FEATURE:
<223> OTHER INFORMATION: forward primer

<400> SEQUENCE: 21
tacaacttct tctcattcg                                                  19

<210> SEQ ID NO 22
<211> LENGTH: 19
<212> TYPE: DNA
<213> ORGANISM: Artificial Sequence
<220> FEATURE:
<223> OTHER INFORMATION: forward primer

<400> SEQUENCE: 22
tccgataagt ccgtacata                                                  19

<210> SEQ ID NO 23
<211> LENGTH: 19
<212> TYPE: DNA
<213> ORGANISM: Artificial Sequence
<220> FEATURE:
<223> OTHER INFORMATION: forward primer

<400> SEQUENCE: 23
gcccaaggat ttcgacaac                                                  19

<210> SEQ ID NO 24
<211> LENGTH: 19
<212> TYPE: DNA
<213> ORGANISM: Artificial Sequence
<220> FEATURE:
<223> OTHER INFORMATION: forward primer

<400> SEQUENCE: 24
ttgtatggtt ttggatgtg                                                  19

<210> SEQ ID NO 25
<211> LENGTH: 19
<212> TYPE: DNA
<213> ORGANISM: Artificial Sequence
<220> FEATURE:
<223> OTHER INFORMATION: forward primer

<400> SEQUENCE: 25
tgttagctgt tttcagtgc                                                  19

<210> SEQ ID NO 26
<211> LENGTH: 19
<212> TYPE: DNA
<213> ORGANISM: Artificial Sequence
<220> FEATURE:
<223> OTHER INFORMATION: forward primer

<400> SEQUENCE: 26
caatagtttt cggcatttt                                                  19

<210> SEQ ID NO 27
<211> LENGTH: 19
<212> TYPE: DNA
<213> ORGANISM: Artificial Sequence
<220> FEATURE:
<223> OTHER INFORMATION: forward primer

<400> SEQUENCE: 27
```

| | |
|---|---|
| gcctaacagt gctgaagaa | 19 |

<210> SEQ ID NO 28
<211> LENGTH: 19
<212> TYPE: DNA
<213> ORGANISM: Artificial Sequence
<220> FEATURE:
<223> OTHER INFORMATION: forward primer

<400> SEQUENCE: 28

| | |
|---|---|
| caaaacaagt ctccacttg | 19 |

<210> SEQ ID NO 29
<211> LENGTH: 19
<212> TYPE: DNA
<213> ORGANISM: Artificial Sequence
<220> FEATURE:
<223> OTHER INFORMATION: forward primer

<400> SEQUENCE: 29

| | |
|---|---|
| ttggagcatt gtcgagtag | 19 |

<210> SEQ ID NO 30
<211> LENGTH: 19
<212> TYPE: DNA
<213> ORGANISM: Artificial Sequence
<220> FEATURE:
<223> OTHER INFORMATION: forward primer

<400> SEQUENCE: 30

| | |
|---|---|
| gataatcact ctctagagt | 19 |

<210> SEQ ID NO 31
<211> LENGTH: 19
<212> TYPE: DNA
<213> ORGANISM: Artificial Sequence
<220> FEATURE:
<223> OTHER INFORMATION: forward primer

<400> SEQUENCE: 31

| | |
|---|---|
| atgcatgcgt tcgtacaaa | 19 |

<210> SEQ ID NO 32
<211> LENGTH: 19
<212> TYPE: DNA
<213> ORGANISM: Artificial Sequence
<220> FEATURE:
<223> OTHER INFORMATION: forward primer

<400> SEQUENCE: 32

| | |
|---|---|
| caagacttat ttctagtgt | 19 |

<210> SEQ ID NO 33
<211> LENGTH: 19
<212> TYPE: DNA
<213> ORGANISM: Artificial Sequence
<220> FEATURE:
<223> OTHER INFORMATION: forward primer

<400> SEQUENCE: 33

| | |
|---|---|
| ccccagtgct cgtcatggt | 19 |

<210> SEQ ID NO 34
<211> LENGTH: 19
<212> TYPE: DNA
<213> ORGANISM: Artificial Sequence

```
<220> FEATURE:
<223> OTHER INFORMATION: forward primer

<400> SEQUENCE: 34
cgtaagagct cgtaagacg                                                  19

<210> SEQ ID NO 35
<211> LENGTH: 19
<212> TYPE: DNA
<213> ORGANISM: Artificial Sequence
<220> FEATURE:
<223> OTHER INFORMATION: forward primer

<400> SEQUENCE: 35
ctgtattttt gccaacttt                                                  19

<210> SEQ ID NO 36
<211> LENGTH: 19
<212> TYPE: DNA
<213> ORGANISM: Artificial Sequence
<220> FEATURE:
<223> OTHER INFORMATION: forward primer

<400> SEQUENCE: 36
gcgataacat ggtgacctc                                                  19

<210> SEQ ID NO 37
<211> LENGTH: 19
<212> TYPE: DNA
<213> ORGANISM: Artificial Sequence
<220> FEATURE:
<223> OTHER INFORMATION: forward primer

<400> SEQUENCE: 37
cacgaatctt aacaatgtg                                                  19

<210> SEQ ID NO 38
<211> LENGTH: 19
<212> TYPE: DNA
<213> ORGANISM: Artificial Sequence
<220> FEATURE:
<223> OTHER INFORMATION: forward primer

<400> SEQUENCE: 38
gttgatccct gcccacggt                                                  19

<210> SEQ ID NO 39
<211> LENGTH: 19
<212> TYPE: DNA
<213> ORGANISM: Artificial Sequence
<220> FEATURE:
<223> OTHER INFORMATION: forward primer

<400> SEQUENCE: 39
aattactggt ggacaacgg                                                  19

<210> SEQ ID NO 40
<211> LENGTH: 19
<212> TYPE: DNA
<213> ORGANISM: Artificial Sequence
<220> FEATURE:
<223> OTHER INFORMATION: forward primer

<400> SEQUENCE: 40
aaatacgcgt tgagaagta                                                  19
```

```
<210> SEQ ID NO 41
<211> LENGTH: 19
<212> TYPE: DNA
<213> ORGANISM: Artificial Sequence
<220> FEATURE:
<223> OTHER INFORMATION: forward primer

<400> SEQUENCE: 41
ccctaactgt tttaactgg                                                  19

<210> SEQ ID NO 42
<211> LENGTH: 19
<212> TYPE: DNA
<213> ORGANISM: Artificial Sequence
<220> FEATURE:
<223> OTHER INFORMATION: forward primer

<400> SEQUENCE: 42
ttatatctat ctttacgtg                                                  19

<210> SEQ ID NO 43
<211> LENGTH: 19
<212> TYPE: DNA
<213> ORGANISM: Artificial Sequence
<220> FEATURE:
<223> OTHER INFORMATION: forward primer

<400> SEQUENCE: 43
tctcaccaat gtggagagg                                                  19

<210> SEQ ID NO 44
<211> LENGTH: 19
<212> TYPE: DNA
<213> ORGANISM: Artificial Sequence
<220> FEATURE:
<223> OTHER INFORMATION: forward primer

<400> SEQUENCE: 44
tgaaaccatt aagcaattt                                                  19

<210> SEQ ID NO 45
<211> LENGTH: 19
<212> TYPE: DNA
<213> ORGANISM: Artificial Sequence
<220> FEATURE:
<223> OTHER INFORMATION: forward primer

<400> SEQUENCE: 45
ttttatttat tcttagggt                                                  19

<210> SEQ ID NO 46
<211> LENGTH: 19
<212> TYPE: DNA
<213> ORGANISM: Artificial Sequence
<220> FEATURE:
<223> OTHER INFORMATION: forward primer

<400> SEQUENCE: 46
tatcaggggt ttctagttt                                                  19

<210> SEQ ID NO 47
<211> LENGTH: 19
<212> TYPE: DNA
<213> ORGANISM: Artificial Sequence
<220> FEATURE:
<223> OTHER INFORMATION: forward primer
```

<400> SEQUENCE: 47
cctgagttat ggagagcac                                                19

<210> SEQ ID NO 48
<211> LENGTH: 19
<212> TYPE: DNA
<213> ORGANISM: Artificial Sequence
<220> FEATURE:
<223> OTHER INFORMATION: forward primer

<400> SEQUENCE: 48
gacaacaact atggattac                                                19

<210> SEQ ID NO 49
<211> LENGTH: 19
<212> TYPE: DNA
<213> ORGANISM: Artificial Sequence
<220> FEATURE:
<223> OTHER INFORMATION: forward primer

<400> SEQUENCE: 49
ccgtatccat gaagacgtt                                                19

<210> SEQ ID NO 50
<211> LENGTH: 19
<212> TYPE: DNA
<213> ORGANISM: Artificial Sequence
<220> FEATURE:
<223> OTHER INFORMATION: forward primer

<400> SEQUENCE: 50
caaaatggct aaagactaa                                                19

<210> SEQ ID NO 51
<211> LENGTH: 19
<212> TYPE: DNA
<213> ORGANISM: Artificial Sequence
<220> FEATURE:
<223> OTHER INFORMATION: forward primer

<400> SEQUENCE: 51
agaaatgcat gagtaaagg                                                19

<210> SEQ ID NO 52
<211> LENGTH: 19
<212> TYPE: DNA
<213> ORGANISM: Artificial Sequence
<220> FEATURE:
<223> OTHER INFORMATION: forward primer

<400> SEQUENCE: 52
gtgtattgtt gtaaataag                                                19

<210> SEQ ID NO 53
<211> LENGTH: 19
<212> TYPE: DNA
<213> ORGANISM: Artificial Sequence
<220> FEATURE:
<223> OTHER INFORMATION: forward primer

<400> SEQUENCE: 53
aaggagatct acccactag                                                19

<210> SEQ ID NO 54

```
<211> LENGTH: 19
<212> TYPE: DNA
<213> ORGANISM: Artificial Sequence
<220> FEATURE:
<223> OTHER INFORMATION: forward primer

<400> SEQUENCE: 54
tcccaatctt ccctacaag                                                19

<210> SEQ ID NO 55
<211> LENGTH: 19
<212> TYPE: DNA
<213> ORGANISM: Artificial Sequence
<220> FEATURE:
<223> OTHER INFORMATION: forward primer

<400> SEQUENCE: 55
tgttaaaaat atttatttt                                                19

<210> SEQ ID NO 56
<211> LENGTH: 19
<212> TYPE: DNA
<213> ORGANISM: Artificial Sequence
<220> FEATURE:
<223> OTHER INFORMATION: forward primer

<400> SEQUENCE: 56
agtcattctt ggttatatt                                                19

<210> SEQ ID NO 57
<211> LENGTH: 19
<212> TYPE: DNA
<213> ORGANISM: Artificial Sequence
<220> FEATURE:
<223> OTHER INFORMATION: forward primer

<400> SEQUENCE: 57
ataaagtttt gtataattc                                                19

<210> SEQ ID NO 58
<211> LENGTH: 19
<212> TYPE: DNA
<213> ORGANISM: Artificial Sequence
<220> FEATURE:
<223> OTHER INFORMATION: forward primer

<400> SEQUENCE: 58
cactagaatt ccgaagggt                                                19

<210> SEQ ID NO 59
<211> LENGTH: 19
<212> TYPE: DNA
<213> ORGANISM: Artificial Sequence
<220> FEATURE:
<223> OTHER INFORMATION: forward primer

<400> SEQUENCE: 59
tttgatgttt gtttacact                                                19

<210> SEQ ID NO 60
<211> LENGTH: 19
<212> TYPE: DNA
<213> ORGANISM: Artificial Sequence
<220> FEATURE:
<223> OTHER INFORMATION: forward primer

<400> SEQUENCE: 60
```

| | |
|---|---|
| tttaaaggat ctgtatgtg | 19 |

<210> SEQ ID NO 61
<211> LENGTH: 19
<212> TYPE: DNA
<213> ORGANISM: Artificial Sequence
<220> FEATURE:
<223> OTHER INFORMATION: forward primer

<400> SEQUENCE: 61

| | |
|---|---|
| aaaaacatgt agtcaaacg | 19 |

<210> SEQ ID NO 62
<211> LENGTH: 19
<212> TYPE: DNA
<213> ORGANISM: Artificial Sequence
<220> FEATURE:
<223> OTHER INFORMATION: reverse primer

<400> SEQUENCE: 62

| | |
|---|---|
| tgaaattgtt tgggacctg | 19 |

<210> SEQ ID NO 63
<211> LENGTH: 19
<212> TYPE: DNA
<213> ORGANISM: Artificial Sequence
<220> FEATURE:
<223> OTHER INFORMATION: reverse primer

<400> SEQUENCE: 63

| | |
|---|---|
| ttacaatatt cggcactcg | 19 |

<210> SEQ ID NO 64
<211> LENGTH: 19
<212> TYPE: DNA
<213> ORGANISM: Artificial Sequence
<220> FEATURE:
<223> OTHER INFORMATION: reverse primer

<400> SEQUENCE: 64

| | |
|---|---|
| tttgacccctt gctaaatgc | 19 |

<210> SEQ ID NO 65
<211> LENGTH: 19
<212> TYPE: DNA
<213> ORGANISM: Artificial Sequence
<220> FEATURE:
<223> OTHER INFORMATION: reverse primer

<400> SEQUENCE: 65

| | |
|---|---|
| tgtgattgtt cgtgaaagt | 19 |

<210> SEQ ID NO 66
<211> LENGTH: 19
<212> TYPE: DNA
<213> ORGANISM: Artificial Sequence
<220> FEATURE:
<223> OTHER INFORMATION: reverse primer

<400> SEQUENCE: 66

| | |
|---|---|
| aaatacccgt tctaacgga | 19 |

<210> SEQ ID NO 67
<211> LENGTH: 19
<212> TYPE: DNA

```
<213> ORGANISM: Artificial Sequence
<220> FEATURE:
<223> OTHER INFORMATION: reverse primer

<400> SEQUENCE: 67
agcaatcttt gtagaagtc                                              19

<210> SEQ ID NO 68
<211> LENGTH: 19
<212> TYPE: DNA
<213> ORGANISM: Artificial Sequence
<220> FEATURE:
<223> OTHER INFORMATION: reverse primer

<400> SEQUENCE: 68
gatgatctct cgggaaaat                                              19

<210> SEQ ID NO 69
<211> LENGTH: 19
<212> TYPE: DNA
<213> ORGANISM: Artificial Sequence
<220> FEATURE:
<223> OTHER INFORMATION: reverse primer

<400> SEQUENCE: 69
atttatgggt tttaagtgc                                              19

<210> SEQ ID NO 70
<211> LENGTH: 19
<212> TYPE: DNA
<213> ORGANISM: Artificial Sequence
<220> FEATURE:
<223> OTHER INFORMATION: reverse primer

<400> SEQUENCE: 70
agtaatcatt tcttaggtc                                              19

<210> SEQ ID NO 71
<211> LENGTH: 19
<212> TYPE: DNA
<213> ORGANISM: Artificial Sequence
<220> FEATURE:
<223> OTHER INFORMATION: reverse primer

<400> SEQUENCE: 71
cttgaaggct taagattat                                              19

<210> SEQ ID NO 72
<211> LENGTH: 19
<212> TYPE: DNA
<213> ORGANISM: Artificial Sequence
<220> FEATURE:
<223> OTHER INFORMATION: reverse primer

<400> SEQUENCE: 72
gttgaatgct tcgtatgtt                                              19

<210> SEQ ID NO 73
<211> LENGTH: 19
<212> TYPE: DNA
<213> ORGANISM: Artificial Sequence
<220> FEATURE:
<223> OTHER INFORMATION: reverse primer

<400> SEQUENCE: 73
gcacatcttt cggtatctc                                              19
```

<210> SEQ ID NO 74
<211> LENGTH: 19
<212> TYPE: DNA
<213> ORGANISM: Artificial Sequence
<220> FEATURE:
<223> OTHER INFORMATION: reverse primer

<400> SEQUENCE: 74
tgtaatgtct gatgaactc                                                19

<210> SEQ ID NO 75
<211> LENGTH: 19
<212> TYPE: DNA
<213> ORGANISM: Artificial Sequence
<220> FEATURE:
<223> OTHER INFORMATION: reverse primer

<400> SEQUENCE: 75
atcaagggct acggattgc                                                19

<210> SEQ ID NO 76
<211> LENGTH: 19
<212> TYPE: DNA
<213> ORGANISM: Artificial Sequence
<220> FEATURE:
<223> OTHER INFORMATION: reverse primer

<400> SEQUENCE: 76
ttggatatgt atcgacgac                                                19

<210> SEQ ID NO 77
<211> LENGTH: 19
<212> TYPE: DNA
<213> ORGANISM: Artificial Sequence
<220> FEATURE:
<223> OTHER INFORMATION: reverse primer

<400> SEQUENCE: 77
agtaagtcgt cctaagggg                                                19

<210> SEQ ID NO 78
<211> LENGTH: 19
<212> TYPE: DNA
<213> ORGANISM: Artificial Sequence
<220> FEATURE:
<223> OTHER INFORMATION: reverse primer

<400> SEQUENCE: 78
ataatttgtc tttatccta                                                19

<210> SEQ ID NO 79
<211> LENGTH: 19
<212> TYPE: DNA
<213> ORGANISM: Artificial Sequence
<220> FEATURE:
<223> OTHER INFORMATION: reverse primer

<400> SEQUENCE: 79
tgagattaat ggcgacgtg                                                19

<210> SEQ ID NO 80
<211> LENGTH: 19
<212> TYPE: DNA
<213> ORGANISM: Artificial Sequence
<220> FEATURE:

-continued

<223> OTHER INFORMATION: reverse primer

<400> SEQUENCE: 80
tttcattcct ttataatag                                                19

<210> SEQ ID NO 81
<211> LENGTH: 19
<212> TYPE: DNA
<213> ORGANISM: Artificial Sequence
<220> FEATURE:
<223> OTHER INFORMATION: reverse primer

<400> SEQUENCE: 81
tttaatgttt aactattta                                                19

<210> SEQ ID NO 82
<211> LENGTH: 19
<212> TYPE: DNA
<213> ORGANISM: Artificial Sequence
<220> FEATURE:
<223> OTHER INFORMATION: reverse primer

<400> SEQUENCE: 82
tgtaatccct atacaatga                                                19

<210> SEQ ID NO 83
<211> LENGTH: 19
<212> TYPE: DNA
<213> ORGANISM: Artificial Sequence
<220> FEATURE:
<223> OTHER INFORMATION: reverse primer

<400> SEQUENCE: 83
ggtaataggt atcgattgg                                                19

<210> SEQ ID NO 84
<211> LENGTH: 19
<212> TYPE: DNA
<213> ORGANISM: Artificial Sequence
<220> FEATURE:
<223> OTHER INFORMATION: reverse primer

<400> SEQUENCE: 84
aatcataact ttgtaactt                                                19

<210> SEQ ID NO 85
<211> LENGTH: 19
<212> TYPE: DNA
<213> ORGANISM: Artificial Sequence
<220> FEATURE:
<223> OTHER INFORMATION: reverse primer

<400> SEQUENCE: 85
aataaatatt gtcgattca                                                19

<210> SEQ ID NO 86
<211> LENGTH: 19
<212> TYPE: DNA
<213> ORGANISM: Artificial Sequence
<220> FEATURE:
<223> OTHER INFORMATION: reverse primer

<400> SEQUENCE: 86
tctaatcttt aagatgtga                                                19

<210> SEQ ID NO 87
<211> LENGTH: 19
<212> TYPE: DNA
<213> ORGANISM: Artificial Sequence
<220> FEATURE:
<223> OTHER INFORMATION: reverse primer

<400> SEQUENCE: 87
gattattatt ttcaaattg                                              19

<210> SEQ ID NO 88
<211> LENGTH: 19
<212> TYPE: DNA
<213> ORGANISM: Artificial Sequence
<220> FEATURE:
<223> OTHER INFORMATION: reverse primer

<400> SEQUENCE: 88
atacagggtt agcgagctg                                              19

<210> SEQ ID NO 89
<211> LENGTH: 19
<212> TYPE: DNA
<213> ORGANISM: Artificial Sequence
<220> FEATURE:
<223> OTHER INFORMATION: reverse primer

<400> SEQUENCE: 89
agttattatt tgttagcgc                                              19

<210> SEQ ID NO 90
<211> LENGTH: 19
<212> TYPE: DNA
<213> ORGANISM: Artificial Sequence
<220> FEATURE:
<223> OTHER INFORMATION: reverse primer

<400> SEQUENCE: 90
ggatatgttt agaaaaaag                                              19

<210> SEQ ID NO 91
<211> LENGTH: 19
<212> TYPE: DNA
<213> ORGANISM: Artificial Sequence
<220> FEATURE:
<223> OTHER INFORMATION: reverse primer

<400> SEQUENCE: 91
ggtcatatat agaaaatag                                              19

<210> SEQ ID NO 92
<211> LENGTH: 19
<212> TYPE: DNA
<213> ORGANISM: Artificial Sequence
<220> FEATURE:
<223> OTHER INFORMATION: reverse primer

<400> SEQUENCE: 92
ttttattttt tacaacgca                                              19

<210> SEQ ID NO 93
<211> LENGTH: 19
<212> TYPE: DNA
<213> ORGANISM: Artificial Sequence
<220> FEATURE:
<223> OTHER INFORMATION: reverse primer

```
<400> SEQUENCE: 93
taggagttgt taggaccgt                                                  19

<210> SEQ ID NO 94
<211> LENGTH: 19
<212> TYPE: DNA
<213> ORGANISM: Artificial Sequence
<220> FEATURE:
<223> OTHER INFORMATION: reverse primer

<400> SEQUENCE: 94
tatcagaagt tgcaattct                                                  19

<210> SEQ ID NO 95
<211> LENGTH: 19
<212> TYPE: DNA
<213> ORGANISM: Artificial Sequence
<220> FEATURE:
<223> OTHER INFORMATION: reverse primer

<400> SEQUENCE: 95
ctgaacctct aatcatcgg                                                  19

<210> SEQ ID NO 96
<211> LENGTH: 19
<212> TYPE: DNA
<213> ORGANISM: Artificial Sequence
<220> FEATURE:
<223> OTHER INFORMATION: reverse primer

<400> SEQUENCE: 96
aggcactggt cgtcaagat                                                  19

<210> SEQ ID NO 97
<211> LENGTH: 19
<212> TYPE: DNA
<213> ORGANISM: Artificial Sequence
<220> FEATURE:
<223> OTHER INFORMATION: reverse primer

<400> SEQUENCE: 97
ggcaataggt gggaagggt                                                  19

<210> SEQ ID NO 98
<211> LENGTH: 19
<212> TYPE: DNA
<213> ORGANISM: Artificial Sequence
<220> FEATURE:
<223> OTHER INFORMATION: reverse primer

<400> SEQUENCE: 98
taacaaatat cgatatcta                                                  19

<210> SEQ ID NO 99
<211> LENGTH: 19
<212> TYPE: DNA
<213> ORGANISM: Artificial Sequence
<220> FEATURE:
<223> OTHER INFORMATION: reverse primer

<400> SEQUENCE: 99
ttttaacgct agttaccca                                                  19

<210> SEQ ID NO 100
<211> LENGTH: 19
```

<210> SEQ ID NO 101
<211> LENGTH: 19
<212> TYPE: DNA
<213> ORGANISM: Artificial Sequence
<220> FEATURE:
<223> OTHER INFORMATION: reverse primer

<400> SEQUENCE: 100
cttgataatt tgagatact                                                19

<210> SEQ ID NO 101
<211> LENGTH: 19
<212> TYPE: DNA
<213> ORGANISM: Artificial Sequence
<220> FEATURE:
<223> OTHER INFORMATION: reverse primer

<400> SEQUENCE: 101
aattaatggt attgattat                                                19

<210> SEQ ID NO 102
<211> LENGTH: 19
<212> TYPE: DNA
<213> ORGANISM: Artificial Sequence
<220> FEATURE:
<223> OTHER INFORMATION: reverse primer

<400> SEQUENCE: 102
aaagatgttt gacaaacgc                                                19

<210> SEQ ID NO 103
<211> LENGTH: 19
<212> TYPE: DNA
<213> ORGANISM: Artificial Sequence
<220> FEATURE:
<223> OTHER INFORMATION: reverse primer

<400> SEQUENCE: 103
tcacagggtt gttgatctt                                                19

<210> SEQ ID NO 104
<211> LENGTH: 19
<212> TYPE: DNA
<213> ORGANISM: Artificial Sequence
<220> FEATURE:
<223> OTHER INFORMATION: reverse primer

<400> SEQUENCE: 104
ttcgacatct tgacatgac                                                19

<210> SEQ ID NO 105
<211> LENGTH: 19
<212> TYPE: DNA
<213> ORGANISM: Artificial Sequence
<220> FEATURE:
<223> OTHER INFORMATION: reverse primer

<400> SEQUENCE: 105
atatattgtt ttcagcgta                                                19

<210> SEQ ID NO 106
<211> LENGTH: 19
<212> TYPE: DNA
<213> ORGANISM: Artificial Sequence
<220> FEATURE:
<223> OTHER INFORMATION: reverse primer

<400> SEQUENCE: 106
tgataatcat gttgacact          19

<210> SEQ ID NO 107
<211> LENGTH: 19
<212> TYPE: DNA
<213> ORGANISM: Artificial Sequence
<220> FEATURE:
<223> OTHER INFORMATION: reverse primer

<400> SEQUENCE: 107
gaagaagttt tccaaggcc          19

<210> SEQ ID NO 108
<211> LENGTH: 19
<212> TYPE: DNA
<213> ORGANISM: Artificial Sequence
<220> FEATURE:
<223> OTHER INFORMATION: reverse primer

<400> SEQUENCE: 108
gcttatgaat cgcaataca          19

<210> SEQ ID NO 109
<211> LENGTH: 19
<212> TYPE: DNA
<213> ORGANISM: Artificial Sequence
<220> FEATURE:
<223> OTHER INFORMATION: reverse primer

<400> SEQUENCE: 109
ttttacccgt gggaaaccc          19

<210> SEQ ID NO 110
<211> LENGTH: 43
<212> TYPE: DNA
<213> ORGANISM: Artificial Sequence
<220> FEATURE:
<223> OTHER INFORMATION: adaptor forward primer

<400> SEQUENCE: 110
ccatctcatc cctgcgtgtc tccgactcag tgagcggaac gat          43

<210> SEQ ID NO 111
<211> LENGTH: 41
<212> TYPE: DNA
<213> ORGANISM: Artificial Sequence
<220> FEATURE:
<223> OTHER INFORMATION: adaptor reverse primer

<400> SEQUENCE: 111
ccactacgcc tccgctttcc tctctatggg cagtcggtga t          41

<210> SEQ ID NO 112
<211> LENGTH: 20
<212> TYPE: DNA
<213> ORGANISM: Artificial Sequence
<220> FEATURE:
<223> OTHER INFORMATION: forward primer

<400> SEQUENCE: 112
gactcagtga gcggaacgat          20

<210> SEQ ID NO 113
<211> LENGTH: 20
<212> TYPE: DNA
<213> ORGANISM: Artificial Sequence

```
<220> FEATURE:
<223> OTHER INFORMATION: reverse primer

<400> SEQUENCE: 113
ctctatgggc agtcggtgat                                                     20

<210> SEQ ID NO 114
<211> LENGTH: 19
<212> TYPE: DNA
<213> ORGANISM: Artificial Sequence
<220> FEATURE:
<223> OTHER INFORMATION: forward barcode sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(9)
<223> OTHER INFORMATION: n is a, c, g, or t
<220> FEATURE:
<221> NAME/KEY: misc_feature
<222> LOCATION: (11)..(14)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t

<400> SEQUENCE: 114
nnnnannnnt nnnnannnn                                                      19

<210> SEQ ID NO 115
<211> LENGTH: 19
<212> TYPE: DNA
<213> ORGANISM: Artificial Sequence
<220> FEATURE:
<223> OTHER INFORMATION: reverse barcode sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(9)
<223> OTHER INFORMATION: n is a, c, g, or t
<220> FEATURE:
<221> NAME/KEY: misc_feature
<222> LOCATION: (11)..(14)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t

<400> SEQUENCE: 115
nnnnannnnt nnnnannnn                                                      19

<210> SEQ ID NO 116
<211> LENGTH: 19
<212> TYPE: DNA
<213> ORGANISM: Artificial Sequence
<220> FEATURE:
<223> OTHER INFORMATION: reverse adaptor sequence end

<400> SEQUENCE: 116
atcaccgact gccatagag                                                      19

<210> SEQ ID NO 117
<211> LENGTH: 160
<212> TYPE: DNA
```

```
<213> ORGANISM: Artificial Sequence
<220> FEATURE:
<223> OTHER INFORMATION: synthetic primer - sample # 1

<400> SEQUENCE: 117
gactcagtga gcggaacgat gctgactggt acggagggtc tcttcgcggg ggcggctcca      60
cggtctcact ctgcacggcc tcgatcttgt aggggatgtt gaggctgccc agcgagaaga    120
gttggaattg tgcccagtgt atcaccgact gcccatagag                           160

<210> SEQ ID NO 118
<211> LENGTH: 160
<212> TYPE: DNA
<213> ORGANISM: Artificial Sequence
<220> FEATURE:
<223> OTHER INFORMATION: synthetic primer - sample # 2

<400> SEQUENCE: 118
gactcagtga gcggaacgat cggcaactat aaacatttgc tcttcatgga gcctccgcac      60
acgtggacgt tctggacgtg caggctgacc tgccagagcc aggcccccgg gagcggaaga    120
gaagcatgtg tgtccatcaa atcaccgact gcccatagag                           160

<210> SEQ ID NO 119
<211> LENGTH: 160
<212> TYPE: DNA
<213> ORGANISM: Artificial Sequence
<220> FEATURE:
<223> OTHER INFORMATION: synthetic primer - sample # 3

<400> SEQUENCE: 119
gactcagtga gcggaacgat gctgactggt acggagggtc tcttcgcggg ggcggctcca      60
cggtctcact ctgcacggcc tcgatcttgt aggggatgtt gaggctgccc agcgagaaga    120
gttggaattg tgcccagtgt atcaccgact gcccatagag                           160

<210> SEQ ID NO 120
<211> LENGTH: 160
<212> TYPE: DNA
<213> ORGANISM: Artificial Sequence
<220> FEATURE:
<223> OTHER INFORMATION: synthetic primer - sample # 4

<400> SEQUENCE: 120
gactcagtga gcggaacgat ctggatggtt caccatgatc tcttcggaac ttggctccag      60
catgggctgt gtaggtgtcc cctgtcatca acctgctcag gccaaaatca gctacgaaga    120
gcataacaag ttcttattct atcaccgact gcccatagag                           160

<210> SEQ ID NO 121
<211> LENGTH: 160
<212> TYPE: DNA
<213> ORGANISM: Artificial Sequence
<220> FEATURE:
<223> OTHER INFORMATION: synthetic primer - sample # 5

<400> SEQUENCE: 121
gactcagtga gcggaacgat cggcaactat aaacatttgc tcttcatgga gcctccgcac      60
acgtggacgt tctggacgtg caggctgacc tgccagagcc aggcccccgg gagcggaaga    120
gaagcatgtg tgtccatcaa atcaccgact gcccatagag                           160
```